United States Patent
Gerbat et al.

(10) Patent No.: US 11,883,152 B2
(45) Date of Patent: Jan. 30, 2024

(54) ESTIMATING CONTACT ANGLE BETWEEN A CATHETER AND TISSUE, AND ASSOCIATED DEVICES, SYSTEMS AND METHODS

(71) Applicant: KONINKLIJKE PHILIPS N.V., Eindhoven (NL)

(72) Inventors: Oran Gerbat, Caesarea (IL); Shlomo Ben Haim, Caesarea (IL); Asi Elad, Caesarea (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 88 days.

(21) Appl. No.: 17/625,988

(22) PCT Filed: Jul. 6, 2020

(86) PCT No.: PCT/EP2020/068921
§ 371 (c)(1),
(2) Date: Jan. 10, 2022

(87) PCT Pub. No.: WO2021/008907
PCT Pub. Date: Jan. 21, 2021

(65) Prior Publication Data
US 2022/0248977 A1  Aug. 11, 2022

(30) Foreign Application Priority Data
Jul. 12, 2019 (EP) ..................... 19186049

(51) Int. Cl.
*A61B 5/00* (2006.01)
*A61B 5/06* (2006.01)
*A61B 5/0538* (2021.01)

(52) U.S. Cl.
CPC ............ *A61B 5/068* (2013.01); *A61B 5/0538* (2013.01); *A61B 5/7235* (2013.01)

(58) Field of Classification Search
CPC ..... A61B 5/0538; A61B 5/068; A61B 5/6885; A61B 5/7235
See application file for complete search history.

(56) References Cited

U.S. PATENT DOCUMENTS

| | | | |
|---|---|---|---|
| 2012/0101539 A1* | 4/2012 | Zhu ........................ | A61N 1/368 607/9 |
| 2016/0143686 A1 | 5/2016 | Tunay | |
| 2019/0336035 A1 | 11/2019 | Dichterman | |

FOREIGN PATENT DOCUMENTS

WO    2016181315 A1    11/2016

OTHER PUBLICATIONS

International Search Report and Written Opinion of PCT/EP2020/068921, dated Aug. 5, 2020.
(Continued)

*Primary Examiner* — Mark D Remaly

(57) ABSTRACT

Systems and methods for determining a contact angle of a catheter relative to tissue are provided. In one embodiment, a system includes a catheter with three or more electrodes, and a processor circuit in communication with the catheter. The processor circuit controls the three or more electrodes to emit a plurality of electrical voltages and to measure the plurality of electrical voltages. Based on the measured electrical voltages, the processor circuit calculates a first interelectrode impedance and a second interelectrode impedance. The processor circuit calculates, for each of a plurality of hypothetical i.e. model angles, a first hypothetical i.e. model contact force and a second hypothetical i.e. model contact force based on the first and second interelectrode impedances. The processor circuit determines and outputs the contact angle of the catheter based on a comparison of the first and second model contact forces calculated for each of the plurality of model angles.

15 Claims, 10 Drawing Sheets

(56) References Cited

OTHER PUBLICATIONS

Van Es, Rene et al. "Novel Method for Electrode-Tissue Contact Measurement with Multi-Electrode Catheters", Europace, vol. 61, No. 3, pp. 765-774, 2017.

* cited by examiner

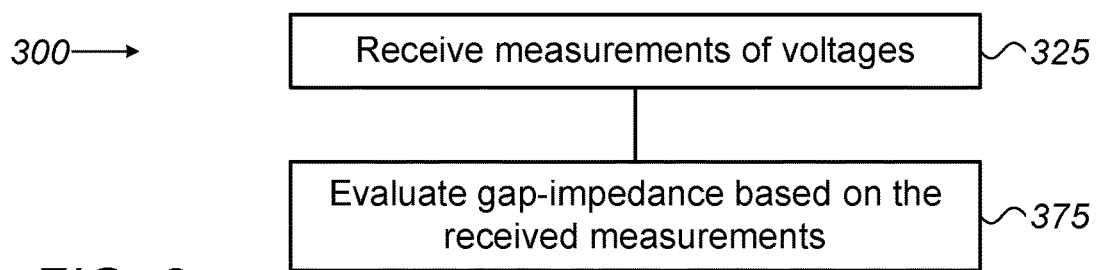
FIG. 3
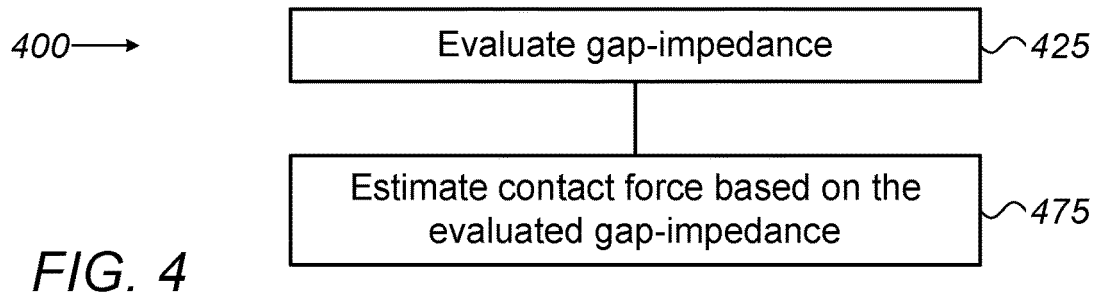
FIG. 4
FIG. 5
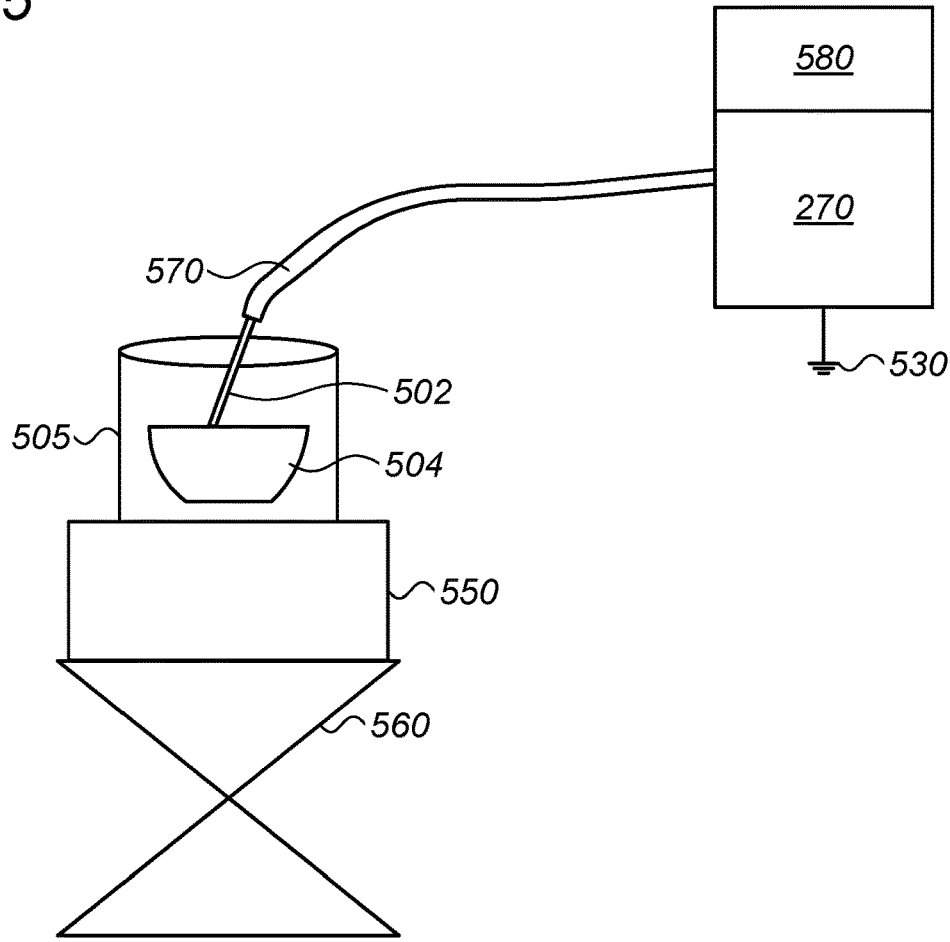

US 11,883,152 B2

ESTIMATING CONTACT ANGLE BETWEEN A CATHETER AND TISSUE, AND ASSOCIATED DEVICES, SYSTEMS AND METHODS

CROSS-REFERENCE TO PRIOR APPLICATIONS

This application is the U.S. National Phase application under 35 U.S.C. § 371 of International Application No. PCT/EP2020/068921, filed on Jul. 6, 2020, which claims the benefit of European Patent Application No. 19186049.3, filed on Jul. 12, 2019. These applications are hereby incorporated by reference herein.

FIELD OF THE INVENTION

The present invention, in some embodiments thereof, is in the field of evaluating impedance based on measurements made at catheter electrodes. Some embodiments are in the field of estimating contact force and contact angle between a catheter and a tissue based on impedance measurements.

BACKGROUND OF THE INVENTION

Publications that may provide technical background to the invention include: the article "measurements of electrical coupling between cardiac ablation catheters and tissue", published in IEEE transcriptions on biomedical engineering, Vol. 61 No 3, pages 765 to 774; the article "novel method for electrode-tissue contact measurement with multi-electrode catheters" published at Europace (2017) 00, 1-8, and the patent application "contact quality assessment by dielectric property analysis" published as WO2016/181315.

US 2016/143686 discloses a method and system for detecting tissue distance, electrode catheter orientation, tissue contact and contact quality, based on measurements of inter-electrode impedance.

SUMMARY OF THE INVENTION

The invention is defined by the claims.

An aspect of some embodiments of the invention includes a method of evaluating electrical impedance of a gap between a first catheter electrode and a second catheter electrode, wherein the first and second catheter electrodes are carried on a same catheter. In some embodiments the method comprises: receiving measurements of electrical voltages; and evaluating the electrical impedance of the gap based on the measurements of the electrical voltages.

In some embodiments, the electrical voltages comprise: a first electrical voltage, which is a voltage difference measured between a reference electrode and the first catheter electrode measured under a first alternating electrical current having a first frequency and flowing through a conductor from an electrical source to the first catheter electrode, and a second electrical voltage, which is a voltage difference measured between the reference electrode and the second catheter electrode under the first alternating electrical current.

In some embodiments, the electrical voltages further comprise: a third electrical voltage, which is a voltage difference measured between the reference electrode and the first catheter electrode measured under a second alternating electrical current flowing through a conductor from an electrical source to the second catheter electrode, and a fourth electrical voltage, which is a voltage difference measured between the reference electrode and the second catheter electrode under the second alternating electrical current.

In some embodiments, the first and second electrical currents have different frequencies. Alternatively, the first and second alternating electrical currents are measured at different times and have the same frequency. In some embodiments, some currents have the same frequency and provided at different times, and some currents have different frequencies and provided at overlapping time periods. In some embodiments, the electrical voltages further comprises: a fifth electrical voltage, which is a voltage difference measured between the reference electrode and the first catheter electrode measured under a third alternating electrical current flowing through a conductor from an electrical source to the first or second catheter electrode, and a sixth electrical voltage, which is a voltage difference measured between the reference electrode and the other one of the two catheter electrodes under the third alternating electrical current.

In some embodiments, the electrical impedance of the gap is evaluated based on measurements of at least one of the electrical currents, in addition to the measurements of the electrical voltages. In some embodiments, the distance between the first catheter electrode and the second catheter electrode is 20 mm or less. In some embodiments, each of the measurements of an electrical potential comprises measurements of a complex electrical potential. In some embodiments, each of the measurements of an electrical current comprises measurements of a complex electrical current. In some embodiments, the catheter is inside a body of a mammal (e.g. an individual, a human, a patient, a person, an animal). In some such embodiments, the reference electrode is attached to an outer skin surface of the individual. In some such embodiments, the reference electrode is attached to an outer skin surface of a leg of the individual. In each one of the above embodiments, evaluating the impedance may include solving equations that are based on the superposition theorem or mathematical equivalents thereof.

An aspect of some embodiments of the invention includes a method of estimating contact force between cardiac tissue of an individual and a catheter carrying a first catheter electrode and a second catheter electrode distanced from each other by a distance smaller than 20 mm. The method comprises: evaluating electrical impedance of a gap between the first catheter electrode and the second catheter electrode; and estimating the contact force based on the impedance evaluated for the gap between the first and second catheter electrodes. In some embodiments, the contact force is estimated based on impedance evaluated in a method as described above.

An aspect of some embodiments of the invention includes a method of estimating contact angle between cardiac tissue of an individual and a catheter carrying a first catheter electrode and a second catheter electrode. The method comprises: evaluating a first electrical resistivity value for a first path going between the first electrode and the reference electrode; evaluating a second electrical resistivity value for a second path between the second electrode and the reference electrode; and estimating the contact angle based on the first and second electrical resistivity values.

In some embodiments, evaluating each one of the first and second electrical resistivity value comprises: receiving measurements of electrical voltages; and evaluating the electrical resistivity of each one of the first and second path based on the measurements of the electrical voltages, wherein the voltage measurements comprise measurements of: a first electrical voltage, which is a voltage difference measured between a reference electrode and the first catheter electrode measured under a first alternating electrical current having a first frequency and flowing through a conductor from an electrical source to the first catheter electrode, and a second electrical voltage, which is a voltage difference measured between the reference electrode and the second catheter electrode under the first alternating electrical current.

In some embodiments, the contact angle is estimated based on a difference between the evaluated resistivities of the first and second path and/or on a ratio between the evaluated resistivities of the first and second path. In some embodiments, the first and second electrical currents have different frequencies. In some embodiments, the first electrical current and a second alternating electrical current are measured at different times and have the same frequency. In some embodiments, the distance between the first catheter electrode and the second catheter electrode is 20 mm or less. In some embodiments, each of the measurements of an electrical potential comprises measurements of a complex electrical potential. In some embodiments, the catheter is inside a body of an individual. In some embodiments, the reference electrode is attached to an outer skin surface of the individual. In some embodiments, the reference electrode is attached to an outer skin surface of a leg of the individual. In some embodiments, evaluating the first electrical resistivity and second electrical resistivity comprises solving equations that are based on the superposition theorem or mathematical equivalents thereof.

An aspect of embodiments of the invention includes a method of estimating contact force between a catheter end and cardiac tissue, wherein the catheter end includes at least three electrodes: a most distal electrode, a least distal electrode, and an intermediate electrode positioned between the most distal electrode and the least distal electrode, the method comprising: estimating a first electrical impedance between the most distal electrode and the intermediate electrode; estimating a second electrical impedance between the intermediate electrode and the least-distal electrode; and estimating the contact force based on each of said first impedance and second impedance to obtain two estimates of the contact force.

In some embodiments, if the contact force estimated based on the first impedance is smaller than a first threshold, the contact force is estimated based on the first impedance alone. In some embodiments, if the contact force estimated based on the second impedance is higher than a second threshold, the contact force is estimated based on the second impedance alone. In some embodiments, if the contact force estimated based on the first impedance is between the first threshold and the second threshold, the contact force is estimated based on an average between a contact force estimated based on the first impedance alone and a contact force estimated based on the second impedance alone. In some embodiments, the average is a weighted average. In some embodiments, evaluating the first impedance is according to a method of evaluating an impedance described above. In some embodiments, evaluating the second impedance is according to a method of evaluating impedance described above.

An aspect of some embodiments of the invention includes an apparatus connectible to a catheter that carries at least a first catheter electrode and a second catheter electrode. In some embodiments, the apparatus includes: a first electrical source configured to generate an alternating electrical current in the first catheter electrode when the apparatus is connected to the catheter; at least one voltmeter configured to measure, when the apparatus is connected to the catheter, a first electrical voltage difference between a reference electrode and the first catheter electrode and a second electrical voltage difference between the reference electrode and the second catheter electrode; and a processor configured to: receive readings from the at least one voltmeter; and evaluate, based on the received readings, an electrical impedance of a gap between the first and second catheter electrodes.

In some embodiments, the apparatus further includes a second electrical source, and the at least one voltmeter comprises a first voltmeter, a second voltmeter, a third voltmeter, and a fourth voltmeter, wherein the first electrical source is configured to generate the alternating current at a first frequency; the second electrical source is configured to generate an alternating current at a second frequency concurrently with the first electrical source; and when the apparatus is connected to the catheter the second electrical source is configured to generate an alternating electrical current in the second catheter electrode; the third voltmeter is configured to measure a third electrical voltage difference between the reference electrode and the first catheter electrode at the frequency generated by the second electrical source; and the fourth voltmeter is configured to measure a fourth electrical voltage difference between the reference electrode and the second catheter electrode at the frequency generated by the second electrical source.

In some embodiments, the electrical impedance of the gap is evaluated based on measurements of at least one of the electrical currents, in addition to the measurements of the electrical voltages. In some embodiments, the apparatus further includes a switch having a first state and a second state, and when the apparatus is connected to the catheter: in the first state the switch connects the electrical source to the first electrode, and in the second state the switch connects the electrical source to the second electrode, and wherein the processor is configured to evaluate the impedance based on readings received from the voltmeters when the switch is at the first state and when the switch is at the second state. In some embodiments, each of the at least one voltmeter is configured to measure a complex voltage. In some embodiments, the apparatus further includes the reference electrode. Optionally, the reference electrode is configured to be attached to an outer skin surface of an individual. In some embodiments, the processor is configured to evaluate the impedance by executing a method of evaluating an impedance described above. In some embodiments, the catheter is an ablation catheter.

In some aspects, an apparatus for determining a contact angle of a catheter relative to tissue comprises a plurality of electrodes positioned on a distal portion of the catheter, and a processor circuit configured to control the catheter electrodes. The processor circuit can control three or more electrodes to obtain electrical measurements to calculate two or more interelectrode impedances associated with two or more electrode pairs of the catheter. The two or more interelectrode impedances are used to calculate a plurality of model contact forces, or hypothetical contact forces, associated with the two or more electrode pairs. The processor can estimate the contact angle by comparing the model contact forces and selecting an angle for which two or more model contact forces are the closest to one another.

According to one embodiment of the present disclosure, a method of determining a contact angle between a catheter and tissue within a body of an individual includes: emitting a first electrical signal from a first electrode of the catheter, emitting a second electrical signal from a second electrode of the catheter, and emitting a third electrical signal from a third electrode of the catheter. The method further includes measuring, using the first electrode, the second electrode, and the third electrode, a plurality of voltages associated with the first, second, and third electrical signals; calculating a first interelectrode impedance based the plurality of voltages; and calculating a second interelectrode impedance based on the plurality of voltages. The method further includes: calculating, for each of a plurality of model angles, a first model contact force and a second model contact force, wherein the first model contact force and the second model contact force are calculated based on the first interelectrode impedance and the second interelectrode impedance, respectively; determining the contact angle based on a comparison of the first model contact force and the second model contact force calculated for each of the plurality of model angles; and outputting, for instance to a display, a representation (e.g. a visual representation) indicating the contact angle.

In some embodiments, emitting the first electrical signal comprises emitting the first electrical signal at a first frequency, emitting the second electrical signal comprises emitting the second electrical signal at a second frequency, emitting the third electrical signal comprises emitting the third electrical signal at a third frequency, and the first, second, and third frequencies are different from each other. In some embodiments, measuring the plurality of voltages comprises: measuring a first voltage using the first electrode at the first frequency; and measuring a second voltage using the first electrode at the second frequency. Further, in some embodiments, measuring the plurality of voltages comprises: measuring a third voltage using the second electrode at the second frequency; and measuring a fourth voltage using the second electrode at the third frequency.

In some embodiments, calculating the first model contact force and the second model contact force comprises calculating the first model contact force and the second model contact force using a relationship that includes the plurality of model angles, the first and second interelectrode impedances, and interelectrode spacing. In some embodiments, determining the contact angle comprises interpolating two or more model angles. In some embodiments, interpolating the two or more model angles comprises applying a weight function to each of the model angles based on a comparison of the first model contact force and the second model contact force. In some embodiments, the catheter comprises an intracardiac electrophysiology catheter, and the first, second, and third electrodes are positioned at a distal portion of the catheter.

According to another embodiment of the present disclosure, an apparatus includes: a processor circuit in communication with a catheter configured to contact tissue within a body of an individual at a contact angle. The processor circuit is configured to control: a first electrode of the catheter to emit a first electrical signal, a second electrode of the catheter to emit a second electrical signal, and a third electrode of the catheter to emit a third electrical signal. The processor is further configured to: control the first electrode, the second electrode, and the third electrode to measure a plurality of voltages associated with the first, second, and third electrical signals; calculate a first interelectrode impedance based on the plurality of voltages; calculate a different, second interelectrode impedance based on the plurality of voltages; calculate, for each of a plurality of model angles, a first model contact force and a second model contact force, wherein the first model contact force and the second model contact force are calculated based on the first interelectrode impedance and the second interelectrode impedance, respectively; determine the contact angle based on a comparison of the first model contact force and the second model contact force calculated for each of the plurality of model angles; and output, for instance to a display in communication with the processor circuit, a representation indicating the contact angle (e.g. a visual representation).

In some embodiments, the processor circuit is configured to control the first electrode to emit the first electrical signal at a first frequency, control the second electrode to emit the second electrical signal at a second frequency, and control the third electrode to emit the third electrical signal at a third frequency. In some aspects, the first, second, and third frequencies are different from each other. In some embodiments, the processor circuit is configured to control: the first electrode to measure a first voltage at the first frequency, and the first electrode to measure a second voltage at the second frequency. In some embodiments, the processor circuit is configured to control the second electrode to measure a third voltage at the second frequency, and control the second electrode to measure a fourth voltage at the third frequency.

In some embodiments, the processor circuit is configured to calculate the first model contact force and the second model contact force using a relationship that includes the plurality of model angles, the first and second interelectrode impedances, and interelectrode spacing. In some embodiments, the processor circuit is configured to determine the contact angle by interpolating two or more model angles. In some embodiments, the processor circuit is configured to interpolate the two or more model angles by applying a weight function to each of the model angles based on a comparison of the first model contact force and the second model contact force. In some embodiments, the catheter comprises an intracardiac electrophysiology catheter, and wherein the first, second, and third electrodes are positioned at a distal portion of the catheter. In one embodiment, a system comprises the apparatus according to one or more of the embodiments described above, and further comprises the catheter comprising the first electrode, the second electrode, and the third electrode positioned at a distal portion of the catheter According to another embodiment of the present disclosure, a computer program product includes: a non-transitory computer-readable medium having program code recorded thereon. The program code includes: code for causing a processor circuit in communication with a catheter to control: a first electrode of the catheter to emit a first electrical signal, a second electrode of the catheter to emit a second electrical signal, and a third electrode of the catheter to emit a third electrical signal. The program code further includes code for causing the processor circuit to control the first electrode, the second electrode, and the third electrode to measure a plurality of voltages associated with the first, second, and third electrical signals. The program code further includes code for causing the processor circuit to calculate a first interelectrode impedance based on the plurality of voltages. The program code further includes code for causing the processor circuit to calculate a different, second interelectrode impedance based on the plurality of voltages. The program code further includes code for causing the processor circuit to calculate, for each of a plurality of model angles, a first model contact force and a second model contact force, wherein the first model contact force and the second model contact force are calculated based on the first interelectrode impedance and the second interelectrode impedance, respectively. The program code further includes code for causing the processor circuit to determine a contact angle between the catheter and tissue based on a comparison of the first model contact force and the second model contact force calculated for each of the plurality of model angles. The program code further includes code for causing the processor circuit to output, to a display in communication with the processor circuit, a visual representation indicating the contact angle.

The computer program product according to an aforementioned embodiment, wherein the program code further comprises code for causing the processor circuit to control: (i) the first electrode to emit the first electrical signal at a first frequency; (ii) the second electrode to emit the second electrical signal at a second frequency; and (iii) the third electrode to emit the third electrical signal at a third frequency, wherein the first, second, and third frequencies are different from each other.

The computer program product according to an aforementioned embodiment, wherein the program code further comprises code for causing the processor circuit to control: (i) the first electrode to measure a first voltage at the first frequency, and (ii) the first electrode to measure a second voltage at the second frequency.

The computer program product according to an aforementioned embodiment, wherein the program code further comprises code for causing the processor circuit to control: (i) the second electrode to measure a third voltage at the second frequency, and (ii) the second electrode to measure a fourth voltage at the third frequency.

The computer program product according to an aforementioned embodiment, wherein the program code further comprises code for causing the processor circuit to calculate the first model contact force and the second model contact force using a relationship that includes the plurality of model angles, the first and second interelectrode impedances, and interelectrode spacing.

The computer program product according to an aforementioned embodiment, wherein the program code further comprises code for causing the processor circuit to determine the contact angle by interpolating two or more model angles.

The computer program product according to an aforementioned embodiment, wherein the program code further comprises code for causing the processor circuit to control the two or more model angles by applying a weight function to each of the model angles based on a comparison of the first model contact force and the second model contact force.

In some embodiments, the program code further comprises code for causing the processor circuit to control: the first electrode to emit the first electrical signal at a first frequency; the second electrode to emit the second electrical signal at a second frequency; and the third electrode to emit the third electrical signal at a third frequency, wherein the first, second, and third frequencies are different from each other. In some embodiments, the program code further comprises code for causing the processor circuit to control: the first electrode to measure a first voltage at the first frequency, and the first electrode to measure a second voltage at the second frequency. In some embodiments, the program code further comprises code for causing the processor circuit to control: the second electrode to measure a third voltage at the second frequency, and the second electrode to measure a fourth voltage at the third frequency.

In some embodiments, the program code further comprises code for causing the processor circuit to calculate the first model contact force and the second model contact force using a relationship that includes the plurality of model angles, the first and second interelectrode impedances, and interelectrode spacing. In some embodiments, the program code further comprises code for causing the processor circuit to determine the contact angle by interpolating two or more model angles. In some embodiments, the program code further comprises code for causing the processor circuit to control the two or more model angles by applying a weight function to each of the model angles based on a comparison of the first model contact force and the second model contact force.

Unless otherwise defined, all technical and/or scientific terms used herein have the same meaning as commonly understood by one of ordinary skill in the art to which the invention pertains. Although methods and apparatuses similar or equivalent to those described herein can be used in the practice or testing of embodiments of the invention, only exemplary methods and/or apparatuses are described below. In addition, the apparatuses, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system". Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 3 is a flowchart of a method of evaluating electrical impedance of a gap between a first catheter electrode carried on a catheter and a second catheter electrode carried on the same catheter according to some embodiments of the invention;

FIG. 4 is a flowchart of a method of estimating contact force between cardiac tissue of an individual and a catheter carrying a first catheter electrode and a second catheter electrode according to some embodiments of the invention;

FIG. 5 is a diagrammatic illustration of an experimental setup for determining parameters characterizing impedance measurement system;

DETAILED DESCRIPTION OF THE EMBODIMENTS

Overview

Figure 1A:
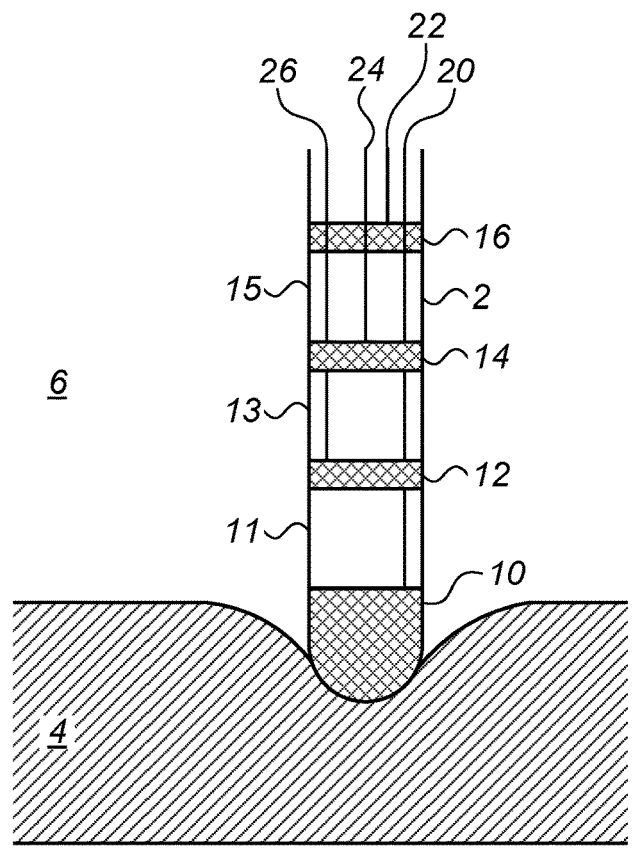
FIG. 1A, FIG. 1B, and FIG. 1C describe a distal end of ablation catheter pressed against tissue at different angles.

Some embodiments of the present invention provide a method of evaluating electrical impedance of a gap between two catheter electrodes. Other embodiments of the present invention provide methods of utilizing a value of such impedance, especially when the electrodes between which the impedance is measured are in the vicinity of an intrabody tissue or pressed against an intrabody tissue of an individual. For example, some embodiments provide method of estimating contact force between the catheter and a tissue to which the catheter is pressed based on impedance evaluation. Some embodiments provide methods of evaluating the angle at which the catheter is pressed to the tissue within the body of an individual, based on such impedance evaluation; and some embodiments provide methods of determining a characteristic of the tissue itself based on such impedance. For example, if the catheter electrodes are in a left atrium of a heart, the impedance may be indicative to the thickness of an atrial wall near the electrodes. In another example, tissue in the vicinity of the electrodes may be characterized as being blood, atrial wall, scarred atrial wall, or a valve.

In addition to the above-mentioned methods, the present invention also provides, in some embodiments thereof, an apparatus for carrying out these methods.

While an aspect of the invention includes a specific method of evaluating the impedance of a gap between two electrodes, it is envisaged that the methods for utilizing the obtained values of the impedance may be carried out also with other methods of evaluating the same impedance, when such methods become available. To the best of the knowledge of the present inventor, there is currently no publicly available method of measuring impedance between two catheter electrodes using only the standard wires that connect the electrodes to electrical sources and/or meters.

An aspect of some embodiments of the present invention includes a method of evaluating electrical impedance for a gap between two catheter electrodes carried by the same catheter. In different embodiments the impedance value may be evaluated at different levels of accuracy, and sometimes may be no more than a rough estimate. The impedance evaluated may be influenced by the environment at which the catheter electrodes are at the time of measurement. Therefore, the value obtained is indicative not only of the gap between the catheter electrodes along the catheter body, but also of the environment around the catheter body.

In some embodiments, in order to evaluate the impedance, an alternating electrical current is generated to run along the catheter to one of the two electrodes, and the potential differences generated in response to this current are measured at each of the electrodes. Each of the potential differences (also referred to herein as voltages) is measured between a respective one of the catheter electrodes and a grounded reference electrode, which may be common to the two catheter electrodes. The reference electrode may be a pad electrode, attached to an outer surface of the skin of the individual, for example, to its leg.

The impedance of the gap between the electrodes is evaluated based on these voltage measurements. In some embodiments, additional information or assumptions is used to evaluate the impedance based on those measurements. The additional information may be, for example, an estimate of the self-impedance of the wires connecting the electrical source to the electrodes. Another example of additional information is an assumption as if an impedance of a path going from one catheter electrode to the reference electrode is equal to the impedance of a path going from the other catheter electrode to the reference electrode. Another example of additional information may be measurement of the alternating electrical current, under which the voltages are measured. Specific methods of evaluating the impedance between the electrodes based on the measured values of the voltages are provided below.

In addition to the first alternating electrical current referred to above, in some embodiments, the method includes generating a second alternating electrical current, to run along the catheter to the other electrode. Thus, in such embodiments, there is one current running to the first electrode, and a second current running to the second electrode. Each current can be generated by a different electrical source: a first electrical source connected to the first catheter electrode, and a second electrical source connected to the second catheter electrode. The additional current allows for three additional measurements: one of the current itself, and two of the voltage at the two electrodes. These additional measurements, wholly or partially, may be used as additional information for evaluating the impedance between the electrodes. Each of these currents are of a frequency of between 1 kHz and 100 kHz, for example, between 5 kHz and 25 kHz, and of a magnitude of 1 mA or less.

Similarly, a third, fourth, or any other number of different currents may be added, allowing for additional measurements, and by this allowing the use of a smaller number of approximations and assumptions, and obtaining more precise impedance evaluations, and/or evaluation of additional impedances in the system.

When two (or more) alternating currents are involved, there are basically two kinds of embodiments: those at which the two currents have different frequencies (referred to herein as spectral methods), and those at which the two currents are generated at different times (referred to herein as time sharing methods). In the spectral methods, the two frequencies may be generated at the same time or at different times, and in any way analyzed as if they don't interact with each other. Simultaneous generation of the two currents is usually more convenient. Also, in time sharing methods different frequencies may be used, but using the same (or similar) frequency is usually more convenient. Yet, in some embodiments, when more than two currents are used, spectral separation may be used between some of them, and time sharing between others. In the following, spectral methods will be discussed in detail, and it is believed that skilled person is able to use the present description to carry out time sharing methods without undue experimentation or applying inventive skills.

As used herein, the term "electrical source" refers to any electrical device configured to supply electrical alternating current. An electrical source may be embodied in a current source, in the sense that it is designed to output the same current irrespective of the voltage difference across it. In other embodiments, the electrical source may be a power source that provides a constant power. In some embodiments, the electrical source may be an unregulated source.

DETAILED DESCRIPTION OF THE DRAWINGS

The present invention, in some embodiments thereof, is in the field of evaluating impedance of catheter electrodes. Some embodiments are in the field of estimating contact force between a catheter and a tissue based on impedance measurements.

Before explaining at least one embodiment of the invention in detail, it is to be understood that the invention is not necessarily limited in its application to the details of construction and/or the arrangement of the components and/or methods set forth in the following description and/or illustrated in the drawings. The invention is capable of other embodiments or of being practiced or carried out in various ways.

Figure 1B:
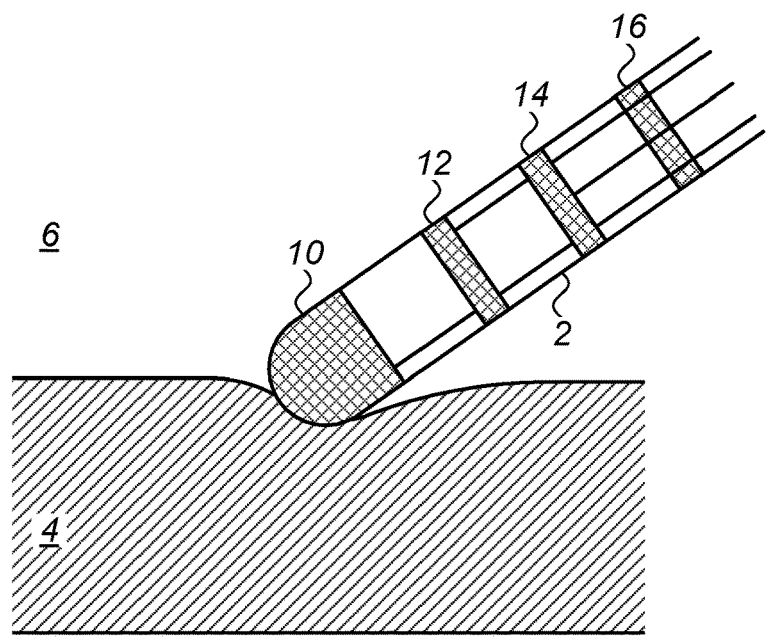
Figure 1C:
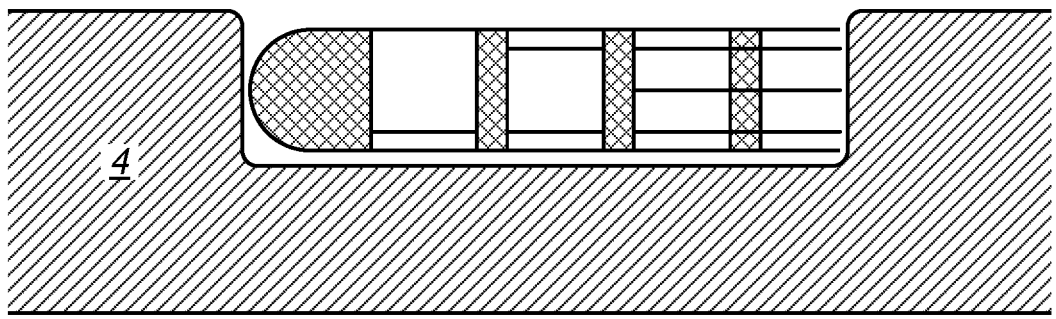

FIGS. 1A to 1C describe a distal end of ablation catheter 2 pressed against tissue 4 at different angles. In FIG. 1A the distal end of the catheter is shown to include four catheter electrodes: a tip electrode (10), which is the most distal electrode, and three ring electrodes 12, 14, and 16. The four electrodes are separated from each other by gaps 11, 13, and 15. Electrode 16 is the least distal electrode, and electrodes 12 and 14 are intermediate electrodes, positioned between the least distal and the most distal electrode. In some commercially available catheters having electrode arrangement similar to that of FIG. 1A, the distance between the tip electrode 10 and the least distal electrode 16 is about 20 mm. In the figure, each electrode is shown to have a respective wire (20, 22, 24, 26) connectible to electrical devices (e.g., electrical source, voltmeter, etc.). In the position shown in FIG. 1A, tip electrode 10 is highly influenced from tissue 4, which nearly entirely surrounds the tip electrode. Catheter electrode 12 is about 5 mm from the tissue, and influenced by the tissue to a much lesser extent, if at all. Catheter electrodes 14 and 16 are about 10 mm and 15 mm from the tissue and may be considered to reside in the blood pool (6). The angle between the tissue and the catheter is about 90 degrees.

In FIG. 1B, same catheter 2 is shown (but the wires are not drawn, for the sake of simplicity). Here, tip electrode 10 is partly in touch with tissue 4 and partly in blood pool 6, electrode 12 is quite close to tissue 4, even if not touching it, and catheter electrodes 14 and 16 are further from the tissue than catheter electrode 12, but much closer than the same electrodes are to the tissue in FIG. 1A.

In FIG. 1C, all the electrodes are in close contact both to tissue 4 and to blood pool 6.

Although only ablation catheters with four electrodes at a distal end thereof are shown, methods as described herein may be used with other kinds of catheters, e.g., lasso catheters with 10 electrodes.

Figure 2A:
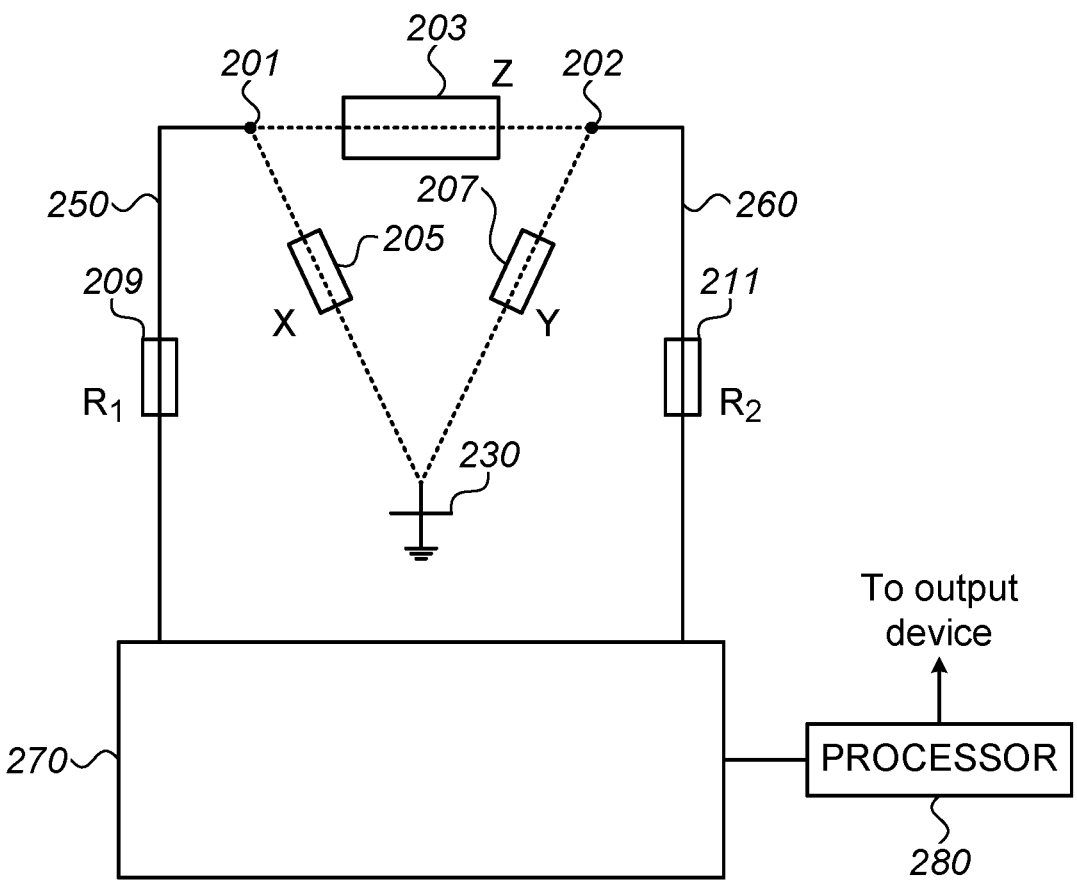
FIG. 2A is a generic illustration of a model for evaluating impedance between two catheter electrodes (and/or between each of the two catheter electrodes and a grounded patch electrode) based on measurements of electrical voltages according to some embodiments of the invention.

FIG. 2A is a generic illustration of a model for evaluating impedance between two catheter electrodes (and/or between each of the two catheter electrodes and a grounded patch electrode) based on measurements of electrical voltages according to some embodiments of the invention. The two catheter electrodes (marked as 201 and 202) may be any two catheter electrodes distanced from each other by up to 20 mm. The distance between the catheter electrodes will determine the ability to attribute the evaluated impedance to a particular location: the more distant the catheter electrodes are from one another, the larger is the region characterized by the evaluated impedance. Thus, in embodiments where impedance of a certain location is of interest, it is preferred that the two electrodes are within that certain location at the time of measurement. In the catheter illustrated in FIG. 1A, for example, the two catheter electrodes may be any two of electrodes 10, 12, 14, or 16 In the remainder of this paragraph the description concentrates on an embodiments wherein catheter electrode 201 stands for tip electrode 10, and catheter electrode 202 stands for electrode 12, however, the methods and apparatuses described are not limited to any specific kind of catheter or to any specific pair of electrodes on the catheter, unless a limitation on the applicability of a certain embodiment is explicitly provided. In particular, the term "first electrode" and "second electrode" may be used to refer to any electrode, and the conventions that the tip electrode is named "first" and the other electrodes are named by their exact order along the catheter are not used in the present disclosure. The model illustrated in FIG. 2A shows conductive wires in full lines, and models mediums along which electrical field propagates as a conductor carrying a load, wherein the conductor is marked with a dashed line, and the load is marked as an empty rectangle. Each such load (203, 205, and 207) is associated with a corresponding impedance (Z, X, and Y, respectively). In particular, the path between electrodes 201 and 202 is modeled by impedance Z, and in the aforementioned embodiment includes tip electrode 10, ring electrode 12, and the medium between them, which includes a portion of tissue 4, blood of blood pool 6, and part of the body of catheter 2. The path between catheter 201 and reference electrode 230 is modeled by impedance X. This path includes mainly tip electrode 10 and body portions through which electrical current runs from tip electrode 10 to the reference electrode, which is not shown in FIG. 1A. The path between catheter electrode 202 and reference electrode 230 is modeled by impedance Y. This path includes mainly catheter electrode 12 and body portions through which electrical current runs from catheter electrode 12 to the reference electrode. In addition, the model shows conducting wires 250 and 260 (corresponding to wires 20 and 22 in the aforementioned embodiment) that connect the catheter electrodes 201 and 202 (10, 12) to an electrical field generator/measurer 270 that generates electrical currents in at least one of conducting wires 250 and 260; and measures voltages at electrodes 201 and 202. Electrical field generator/measurer 270 is also referred to herein as electrical generator/measurer 270. Electrical generator/measurer 270 includes at least one electrical source and at least one voltmeter, as described in more detail in connection with FIGS. 2B to 2D. Conductive wires 250 and 260 go from electrical generator/measurer 270 to the catheter electrode through the catheter itself, and thus may be influenced by the bodily environment through which the catheter runs from outside the body into the heart (or other tissue to be monitored and/or treated by the catheter). Therefore, these conductors are also marked in the model as being loaded with loads (209 and 211) associated with impedances R1 and R2. FIG. 2A also shows that each of the catheter electrodes is connected via the individual's body to a grounded patch electrode 230. The readings of the measurement device(s) in electrical generator/measurer 270 are outputted from the electrical generator/measurer to a processor 280, which processes the measurements to provide evaluation of impedance values for impedance Z, X, Y, R1 and/or R2. In some embodiments, processor 280 also estimates other parameters (for example, contact force) based on the evaluation of one or more of the impedances. The evaluations and/or estimations made by the processor may be outputted to an output device, for example, a visual display, audial display, etc. In practice, the processor may reside inside the electrical generator/measurer, but in some embodiments it is a separate device connected to the electrical generator/measurer by data communication, which may be wired or wireless, and in some embodiments may go through the Internet.

Figure 2B:
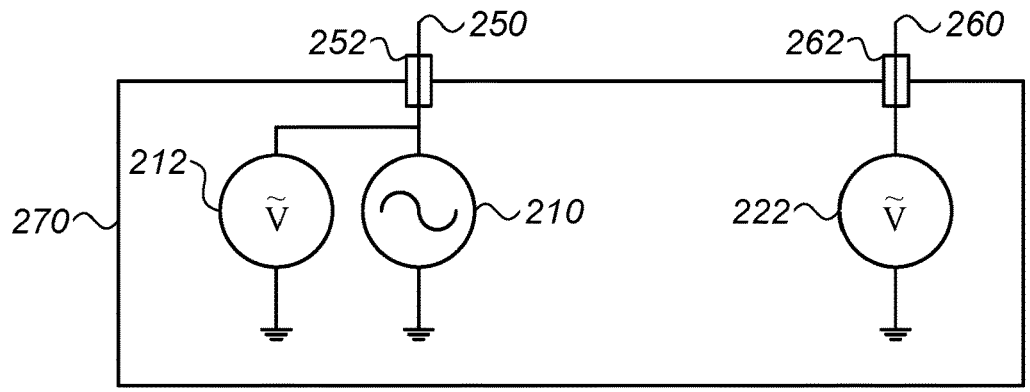
FIG. 2B, FIG. 2C, 2D, and FIG. 2E are schematic illustrations of electrical generator/measurers according to some embodiments of the invention.

FIG. 2B is a schematic illustration of electrical generator/measurer 270 according to some embodiments of the invention. In this embodiment, the electrical generator/measurer includes input/output ports 252 and 262 for connecting devices inside the electrical generator/measurer to wires leading to electrodes 201 and 202. Additional ports (not shown) may be provided to allow connecting other catheter electrodes to the electrical generator/measurer. For example, in some embodiments, measurements of impedances between two or more pairs of catheter electrodes may be carried out simultaneously, and electrical generator/measurer 270 may send and/or receive signals from each of the catheter electrodes members of these two or more pairs of catheter electrodes. The present description provides ample detail on measuring impedance between two electrodes, and the same apply, mutatis mutandis, to measuring impedances between other and/or additional pairs of catheter electrodes, concurrently or not.

Electrical generator/measurer 270 includes an electrical source 210, which may include a voltage source, or a current source (which may be a voltage source connected to a large resistor, e.g., a 100 kilo-ohm resistor). In some embodiments, electrical source 210 may also include an amperemeter (not shown) configured to measure the current provided by the electrical source. The amperemeter is not shown explicitly, as it is usually integral to commercially available current sources. Current generated by electrical source 210 runs to catheter electrode 201 (see FIG. 2A) through conducting wire 250 of the catheter.

A voltage difference between catheter electrode 201 and grounded patch electrode 230 is measured by a voltmeter 212 at least at the time the electrical source is active (in other words, under the current generated by source 210), so the voltage difference is mainly a result of the current provided by electrical source 210.

Voltmeter 222 measures the potential difference between catheter electrode 202 and reference electrode 230 under the current generated by electrical source 210. It is noted that the voltages at both electrodes are measured under the same current. In some embodiments, voltmeter 222 may be omitted, and instead, a switch (not shown) may connect voltmeter 212 once to catheter electrode 201 and once to catheter electrode 202, to obtain the two voltage values.

Readings of the voltages at catheter electrodes 201 and 202 are transmitted to processor 280, which is pre-programmed to evaluate impedance Z based on the received readings. To this end, processor 280 may run a program that solves equations that connect between the supplied current, measured voltages, and the various impedances. The equations may provide a deterministic relation between the various measurements, unknowns, and items of additional information. In some embodiments, the equations may be solved analytically, numerically, or by machine learning methods. The equations are preferably based on a physical model, for example, they may be based on Kirchhoff's Laws or the superposition theorem, or may be any mathematical equivalent of the equations resulting from the superposition theorem. Two sets of equations are considered to be mathematical equivalents of each other if standard mathematical methods can transform one set of equations to the other, or if the two sets of equations solve the same physical problem under the same assumptions. The equations may describe the current distribution between the wires connecting the first and second electrodes to electrical generator/measurer 270, the path between the two electrodes, and the paths between each electrode and the ground electrode. Using the measurements provided by electrical generator/measurer 270 in the embodiment illustrated in FIG. 2B, the number of unknowns in such equations is 6 (the current, and 5 impedances: R1, R2, X, Y, and Z), and the number of measurements is only two (the voltage at each of electrode 201 and 202). In some embodiments, the current is also measured, so the number of unknowns is 5 and the number of measurements is 3. Regardless of whether the current is measured or not, additional information is used in order to solve the equations. This additional information contains, in some embodiments, the current supplied by electrical source 210, assumed values for R1 and R2, and an approximating assumption that X=Y.

Sources for this additional information may be found as follows. The current supplied by electrical source 210 may be known, as the electrical source is controlled and calibrated in manufacture, and ideally supplies the same current irrespective of the rest of the circuit. Alternatively or additionally, the current may be measured.

The approximation that X=Y appears reasonable considering the small distance between electrodes 201 and 202, in relation to the long way there may be from the catheter electrodes to the reference electrode. For example, in the aforementioned embodiment, where electrodes 201 and 202 correspond to electrodes 10 and 12 of FIG. 1A, the distance between the electrodes may be between 1 and 3 mm. In other embodiments, (e.g., where electrodes 201 and 202 correspond to electrodes 10 and 16 of FIG. 1A) this distance may be as large as 20 mm. On the other hand, the distance to the reference electrode may be around half a meter. For example, in some embodiments tissue 4 is at the individual's heart, and the reference electrode is attached to the individual's leg. In such embodiments, the distance between the catheter electrode and the reference electrode may be between about 40 and about 60 cm (depending, inter alia, on the dimensions of the individual). Thus, the distance between the two catheter electrodes may be 100 times shorter than the distance between the catheter electrodes and the reference electrode, and the assumption that X and Y are approximately the same may be reasonable.

Impedances R1 and R2 may be neglected altogether, considering they are mainly impedances of conducting wires. However, the inventor found that considering them may add significantly to the accuracy of the results. Information regarding them may be obtained from other measurements, e.g., of the kind discussed in the context of FIG. 2C, below, or from electromagnetic simulations. Regardless of the basis for assuming certain values for R1 and R2, an approximation that R1 is equal to R2 may be reasonable, as the two wires go through substantially the same medium and along substantially the same way along the catheter.

Thus, additional information used for solving the equations based on the measurements provided by electrical generator/measurer 270 in its configuration depicted in FIG. 2B is available, and the impedance of the gap between electrodes 201 and 202 may be evaluated based on the voltage differences between the reference electrode and electrodes 201 and 202.

Figure 2C:
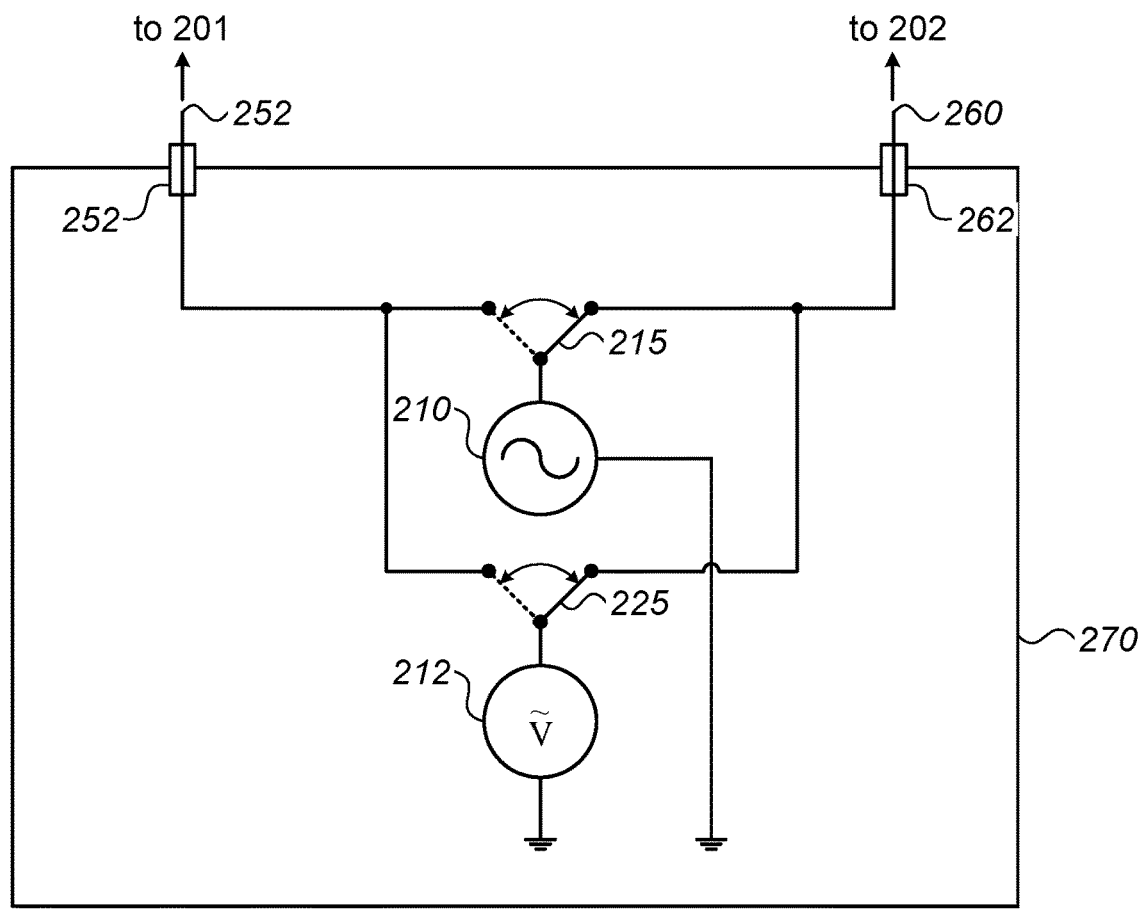

FIG. 2C is a schematic illustration of electrical generator/measurer 270 according to some embodiments of the invention. The configuration of electrical generator/measurer 270, illustrated in FIG. 2C allows for using two currents, having the same frequency but flowing at different times and to different catheter electrodes, for evaluation of the impedance Z. For this, electrical source 210 is connected either to catheter electrode 201 (through wire 250) or to catheter electrode 202 (through wire 260), depending on the state of switch 215. Switch 215 has two states: in one of them (marked with dashed line) the electrical source is connected to wire 250, and in the other (marked with full line)—to wire 260. Similarly, voltmeter 212 is connected to catheter electrode 201 or 202 according to the state of switch 225. Switch 225 has two states: in one of them (marked with dashed line) the voltmeter is connected to wire 250, and in the other (marked with full line)—to wire 260. In operation, the two switches are synchronized (e.g., by processor 280) so that switch 215 stays in one state while switch 225 moves once between its two states, and then switch 215 changes state.

Figure 2D:
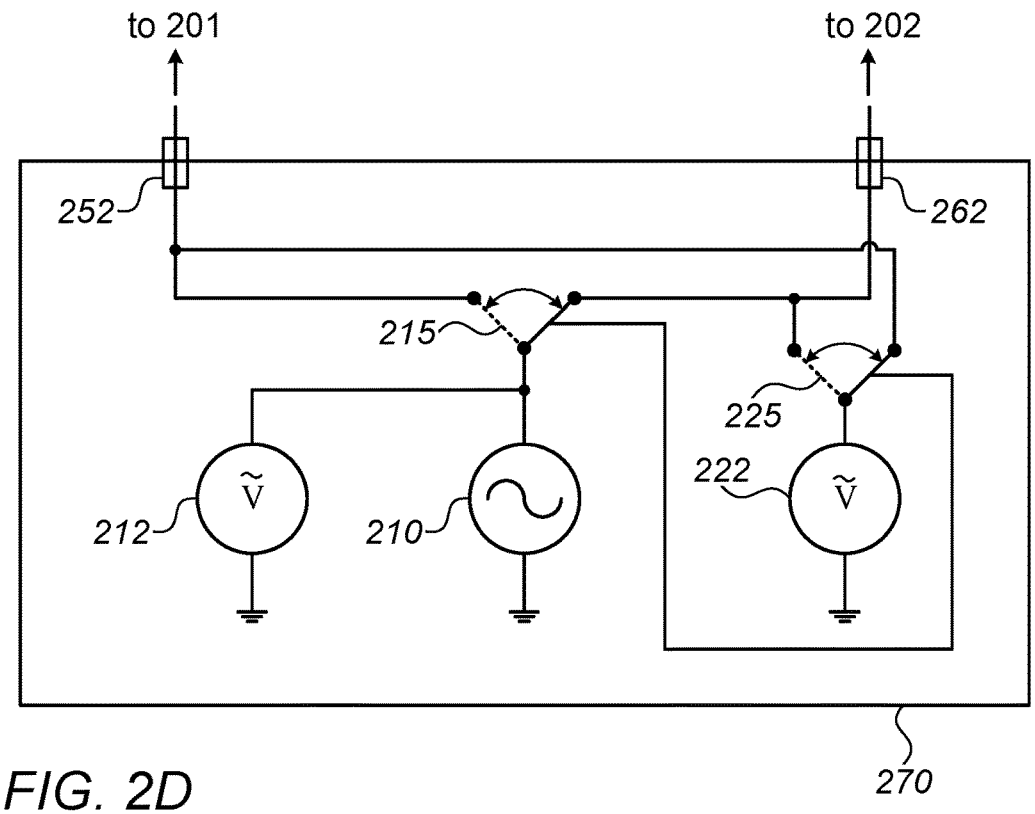

FIG. 2D is a schematic illustration of electrical generator/measurer 270 according to some embodiments of the invention. The configuration of electrical generator/measurer 270, illustrated in FIG. 2D, like that illustrated in FIG. 2C, allows for using two currents, having the same frequency but flowing at different times and to different catheter electrodes, for evaluation of the impedance Z. However, in FIG. 2D the measurement may be faster, in the cost of adding a voltmeter to the generator/measurer. In particular, the output of electrical source 210 is permanently connected to a voltmeter 212. Electrical source 210 is also connected to switch 215, switching the electrical source between electrode 201 and electrode 202, similarly to switch 215 in FIG. 2C. Similarly, voltmeter 222 is connected to catheter electrode 201 or 202 according to the state of switch 225. In operation, the two switches are synchronized so that in each even step the switches are connected as provided in the figure (i.e the electrical source and voltmeter 212 are connected to electrode 202, and voltmeter 222 is connected to electrode 201) and each odd step both switches change states (i.e., the electrical source and voltmeter 212 are connected to electrode 201 and voltmeter 222 is connected to electrode 202). This way, at each step the current source is connected to a different electrode and the voltage is measured at both electrodes.

Figure 2E:
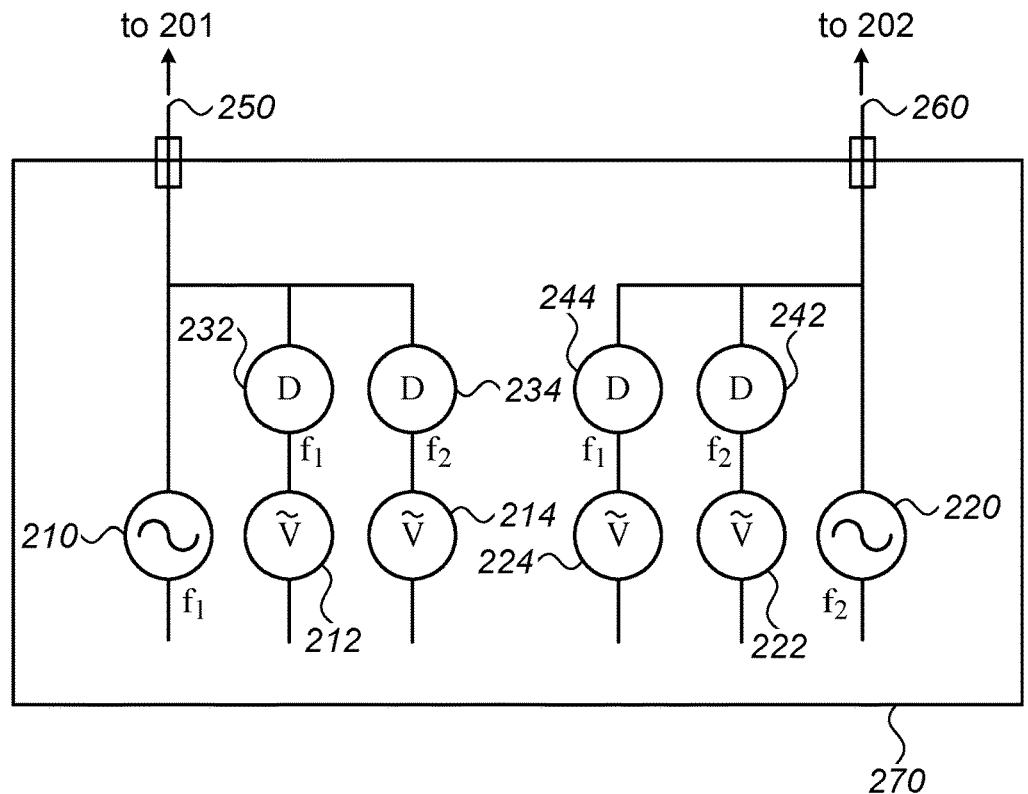

FIG. 2E is a schematic illustration of electrical generator/measurer 270 according to some embodiments of the invention. Like the configuration of electrical generator measurer 270 illustrated in FIGS. 2C and 2D, the configuration illustrated in FIG. 2E allows for using two currents for evaluation of the impedance Z. However, in FIG. 2E the two currents may flow concurrently, (i.e., at overlapping time periods), and the frequencies of the two currents are mutually different. Accordingly, in the configuration of FIG. 2E, a second electrical source, 220, is provided, and connected to the second catheter electrode 202, so that each catheter electrode is connected to a corresponding electrical source. The currents generated by electrical sources 210 and 220 may be of different frequencies, and each of the voltmeters may be configured to measure voltages only in one of these frequencies. For example, each voltmeter may be connected to the corresponding catheter electrode via a demultiplexer (e.g. a correlator). The demultiplexers are marked in the figure by the letter D, and numbered, 232, 234, 242, and 244). The demultiplexer receives as input a signal combining the two frequencies, and outputs mainly the signal component having one frequency. Thus, in one example, voltmeter 212 measures the voltage at catheter electrode 201 at the frequency of the current generated by electrical source 210 (e.g., because demutliplexer 232 multiplies the input signal by a signal having the same frequency as generated by electrical source 210), and voltmeter 214 measures the voltage at catheter electrode 201 at the frequency of the current generated by electrical source 220 (e.g., because demutliplexer 234 multiplies the input signal by a signal having the same frequency as generated by electrical source 220). In the same example, voltmeter 222 measures the voltage at catheter electrode 202 at the frequency of the current generated by electrical source 220, and voltmeter 224 measures the voltage at catheter electrode 202 at the frequency of the current generated by electrical source 210. The frequency that each demultiplexer transfers to the voltmeter connected thereto is marked in the figure. As can be seen, each electrode is connected to voltmeters measuring voltages at each of the frequencies. In some embodiments, there may be more frequencies. For example, four frequencies may be provided, e.g., by four electrical sources connected to corresponding four electrodes. The impedance between two electrodes may then be evaluated for each of four frequencies. In some embodiments, the electrical source may be of variable frequency, and more than two frequencies may be used even with catheters having only two electrodes.

In some embodiments, the two frequencies used in the configuration of FIG. 2E (or in other embodiments utilizing different frequencies) may be relatively close to each other, so the frequency-dependence of the various impedances may be neglected. In some embodiments, the two frequencies are different from each other, and the frequency dependence of the various impedances may be considered in solving the equations. For example, the real part of the impedance may be assumed to be frequency-independent, and the imaginary part of each impedance may be described as a multiple of the frequency, e.g., $$Im(Z) = C_Z f,$$

where $C_Z$ is a real coefficient to be found by solving the equations, and f is the frequency. Similar expressions may be written for the imaginary parts of impedances R1, R2, X, and Y.

Each of the configurations illustrated in FIGS. 2D and 2E adds at least two measurements to the measurements available the configuration illustrated in FIG. 2B: the voltages at catheter electrodes 201 and 202 under the current generated by electrical source 220. Thus, the amount of additional information used for finding Z out of the measurements decreases. In some embodiments, the current supplied by electrical source 220 is known, X and Y are allowed to be different, and the value of R1 and R2 (which are assumed to be the same, as explained above) is found from the measurements.

In some embodiments, additional currents, each at a different frequency (or time slot) may be used to add more measurements and decrease the need for additional information or assumptions. If the number of measurements is larger than the number of unknowns, the equations may be solved using different sub-sets of the measurements to gain information on the accuracy of the obtained values for the various impedances.

While FIGS. 2B, 2C, 2D, and 2E show configurations of electrical generator/measurer 270 for evaluating impedance between two electrodes, in some embodiments, electrical generator/measurer 270 is configured to measure voltages for evaluating impedances between different more pairs of electrodes. For example, for catheter electrodes illustrated in FIG. 1A, electrical generator/measurer 270 may be configured to evaluate the impedance between one or more of the following catheter electrode pairs: 10 and 12, 10 and 14, 10 and 16, 12 and 14, 12 and 16, 14 and 16.

FIG. 3 is a flowchart of a method 300 of evaluating electrical impedance of a gap between a first catheter electrode (e.g., 10) carried on a catheter and a second catheter electrode carried on the same catheter (e.g., catheters 10 and 12 of catheter 2). The impedance evaluated (that is, the impedance associated with the gap) may be the impedance of a hypothetical load connected between the two electrodes, for example, hypothetical load 203. However, the two electrodes are not necessarily neighboring electrodes. For example, in the embodiments shown in FIG. 1A, the two electrodes can be the neighboring electrodes 10 and 12 or 12 and 14 or 12 and 16, or non-neighboring electrodes 10 and 14, 10 and 16, or 12 and 16. It is noted that the gap is not a conductor, although in some cases it may include conducting portions. For example, electrode 12 may be conducting and may make part of the gap between electrodes 10 and 14, but the current running in the gap does not run in a conductor. The term "evaluating" is used herein to refer to an action of associating a value. While it is desirable that the associated value is as close as possible to the actual value of the impedance, there is no guarantee as to the difference between the actual value and the associated value. For example, different embodiments may provide evaluations of different qualities.

Method 300 comprises step 325 of receiving measurements of electrical voltages; and step 375 of evaluating the electrical impedance of the gap based on the received measurements of the electrical voltages. In some embodiments, the received measurements include electrical voltages read at electrodes 201 and 202 when electrical source 210 generates current. In some embodiments, the received measurements include electrical voltages read at electrodes 201 and 202 when electrical source 220 generates current. The electrical sources may generate the currents concurrently (at different frequencies) or at different, non-overlapping, time periods.

Regarding Step 325

The measurements may be taken, for example, by voltmeters 210 and 220. In some embodiments, the data is received in step 325 by a processor configured to receive data indicative of results of the measurements. In some embodiments, the processor forms part of electrical generator/measurer 270. In other embodiments, the processor is processor 280. In some embodiments, the measurements may be received off-line, for example, from a log file of a catheterization operation carried out before method 300 began. In some embodiments, the measurements are received in real time, that is, when the catheter is inside a body of an individual. As used herein, the term "processor" is used to describe any electric circuit that performs a logic operation on input or inputs. For example, a processor may include one or more integrated circuits, microchips, microcontrollers, microprocessors, all or part of a central processing unit (CPU), graphics processing unit (GPU), digital signal processor (DSP), field-programmable gate array (FPGA) or other circuits suitable for executing instructions or performing logic operations. The instructions executed by the processor may, for example, be pre-loaded into a memory unit integrated with or embedded into the processor or may be stored in a separate memory unit, such as a RAM, a ROM, a hard disk, an optical disk, a magnetic medium, a flash memory, other permanent, fixed, or volatile memory, or any other mechanism capable of storing instructions for the controller. The separate memory unit may or may not be a part of the processor. The processor may be customized for a particular use, or can be configured for general-purpose use and can perform different functions by executing different software.

The term "processor" encompasses one or more processors. If more than one processor is employed, all may be of similar construction, or they may be of differing constructions electrically connected or disconnected from each other. They may be separate circuits or integrated in a single circuit. When more than one processor is used, they may be configured to operate independently or collaboratively. They may be coupled electrically, magnetically, optically, acoustically, mechanically or by other means permitting them to interact.

As used herein, if a machine (e.g., a processor) is described as "configured to" perform a particular task (e.g., configured to carry out steps of a particular method), the machine includes components, parts, or aspects (e.g., software) that enable the machine to perform the particular task. In some embodiments, the machine may perform this task during operation. Similarly, when a task is described as being done "in order to" establish a target result then, at least in some embodiments, carrying out the task accomplishes the target result.

Unless otherwise is stated, all voltages and currents referred to herein are alternating, so they can be mathematically represented by complex numbers, having a real part and an imaginary part, or, equivalently, an absolute value and a phase. However, in some embodiments, the measurements do not necessarily measure all the characteristics of the measured quantity. For example, the measurements may be of the real part only, of the absolute value only, or of the full complex value, e.g., absolute value and phase. In the present description and claims, when it is recited that a measurement is of a complex quantity (e.g., voltage or current), the recitation is intended to emphasize that all the characteristics of the measured quantity (i.e., real and imaginary or absolute value and phase) are measured.

A first electrical voltage, the measurement thereof is received in step 325, is a voltage difference between a reference electrode (e.g., 230) and the first catheter electrode (e.g., 10). The first electrical voltage is measured under an alternating electrical current, that is, when an alternating current is running through the first catheter electrode. The alternating electrical current is generated by a source of alternating current. In some embodiments, the source is a current source, in the sense that it is designed to output the same current irrespective of the voltage difference across it. In other embodiments, the source may be a power source that provides a constant power. In such embodiments, it is difficult to provide a good estimate of the current provided by the source without measuring it, so real-time measurement of this current may be more important than in embodiments where the source is a current source.

The source of the first alternating current is connected to the first catheter electrode via a conductor running along and inside the catheter (e.g., conductor 20), so that the current flows directly to the first catheter electrode, and then might split so that part thereof flows through the gap to the second catheter electrode. Another part of the alternating electrical current flows to the reference electrode (e.g., 230) through the individual's body. The effect of the individual's body on the latter part of the current is modeled in FIG. 2A as a load 205, having impedance X. The effect of the body on the flow from the source to the electrode through the conductor is modeled in FIG. 2A as load 207, having impedance R1.

The second electrical voltage used for evaluating impedance Z of load 203 according to method 300 is a voltage difference between the reference electrode (e.g., 230) and the second catheter electrode (12) measured under the same alternating electrical current, under which the first voltage difference is measured.

Regarding Step 375

As used herein, the term "evaluate based on X" means evaluate in a process that relies on a value associated with X. It is noted, however, that the evaluation process may rely on additional values. For example, in step 375, the electrical impedance of gap 203 is evaluated based on the measurements of the first and second electrical voltages. Carrying out such evaluation may include, in some embodiments, finding a value of a function $f$ $$Z = f(V_1, V_2, \text{other information})$$

Wherein $V_1$ is the voltage measured at the first catheter electrode, $V_2$ is the voltage measured at the second catheter electrode, and the other information may include values of parameters, equations presumed to represent acceptable approximations, etc. A value associated with X is not necessarily the "true" value of X, but may be any value measured or approximated to represent a true value of X, whether this representation is accurate or not. For example, the function $f$ may be a parametric function, where the values of R1, R2 are parameters, and the other information may include values associated with these parameters. Additionally or alternatively, the other information may include an equation that X and Y are equal to each other, etc.

As mentioned above, the impedance between the two electrodes may be used for estimating various parameters. In the following, methods for estimating contact force, and contact angle based on physical models are described in detail.

Contact Force

FIG. 4 is a flowchart of a method 400 of estimating contact force between cardiac tissue of an individual (e.g., tissue 4) and a catheter (e.g., catheter 2) carrying a first catheter electrode (e.g., catheter electrode 10) and a second catheter electrode (e.g., catheter electrode 12). Method 400 may be carried out by a processor connected to a catheterization system that includes a catheter (e.g., catheter 2), reference electrode (e.g., 230) electrical sources (e.g., 210, 220) and voltmeters (e.g., 212, 214, 222, and/or 224).

Method 400 comprises step 425 of evaluating electrical impedance of a gap between the first catheter electrode and the second catheter electrode. This impedance evaluation is optionally in accordance with the methods described above. However, should other methods of evaluating the impedance of said gap become available, method 400 may also utilize evaluations obtained with these other methods.

Method 400 also includes step 475, of estimating the contact force based on the impedance evaluated for the gap between the first and second catheter electrodes.

In some embodiments, step 475 may rely on parameters characterizing the system at which the impedance measurements were made, for example, the catheter used, the currents generated for the measurements, etc. These parameters may be measured in advance, e.g., during manufacture of the system, and provided to a processor carrying out method 400 as input. In some embodiments, a user provides input indicative of the kind of catheter to be used (e.g., Smart-touch by Biosense-Webster), and a memory accessible to the processor includes a lookup table providing for each catheter its own set of parameters.

FIG. 5 is a diagrammatic illustration of an experimental setup for determining parameters characterizing impedance measurement system. The experimental setup includes a catheter 502 (which may be similar to catheter 10 of FIG. 1A) touching tissue 504, which may be a tissue of a porcine, an artificial tissue replacement such as open cell sponge, or any other reference tissue used for characterizing the system. Tissue 504 is in a vessel 505, full of saline solution 506 that mimics blood pool 6 of FIG. 1A. Catheter 502 is connected to an electrical generator/measurer 270 via wires 570. The electrical generator/measurer provides measurements to be analyzed and displayed. Optionally, the electrical generator/measurer 270 includes electrical sources and voltmeters as illustrated in any one of FIGS. 2B to 2D, and a processor for carrying out method 300 based on measurements made by the aforementioned voltmeters and additional information available to the processor in a memory accessible thereto. The electrical generator/measurer is also connected to a grounded reference electrode 530, Vessel 505 stands on a weight 550, which stands on a jack 560. Lowering jack 560 reduces the contact force between catheter 502 and tissue 504, and lifting the jack increases the contact force. The weight measures the contact force. The weight may be zeroed with the jack lowered so that the catheter does not touch the tissue.

To obtain the parameters characterizing the system, the jack is moved to different height levels, and in each height level, the weight and the impedance readings (e.g., shown in display 580) are recorded. A parametric function fitting optimally between the absolute impedance readings and the contact force readings is obtained using, e.g., a standard fitting procedure, and the best fitting parameters are recorded as the parameters characterizing the system.

The inventors found that for the system they worked with, the contact force readings were best fitted to the impedance readings through the following parametric function:

$$CF = b|(\|Z\| - \|B\|)|^\alpha$$

Wherein CF is the contact force (e.g., in grams), $\|Z\|$ is the absolute value of the impedance between two electrodes of catheter 502, $\|B\|$ is the absolute value of the impedance between the same two electrodes of catheter 502 when the catheter is in the saline but not touching the tissue, and a and b are parameters characterizing the system.

In some embodiments, to evaluate the contact force between a catheter and a tissue, the absolute value of the impedance between to electrodes on the catheter is evaluated during contact and with no contact, and the above parametric function is used (with the values for a and b found in the experimental setup of FIG. 5) to evaluate the contact force.

In other examples, the parameters of the system are found using different experimental setups. For example, during a catheterization process for treating an individual, contact force is measured with a commercially available contact force sensor (e.g., as provided with Smarttouch™ catheter sold by Biosense-Wester, or TactiCath by St. Jude Medical), and at the same time, the impedance is measured. A function that provides a best fit between the measured contact force values and the evaluated impedance values is used to estimate the contact force from impedance values in other catheterization processes, carried out in absence of a commercially available contact force sensor.

In some embodiments, the catheter is used also for tissue ablation, by transmitting RF energy to the tissue via the tip electrode. This RF transmission may generate a lot of noise in the evaluation of the impedance between the tip electrode and any other catheter electrode. Therefore, in some such embodiments, the contact force during ablation is estimated based on impedance evaluated for a gap between two non-tip catheter electrodes. This way, the noise introduced by the RF transmitted for the ablation has a smaller effect on the contact force measurement.

Contact Force Between Tissue and a Collapsing Catheter

Some catheters are designed to collapse under some contact force to omit puncturing the tissue by a catheter tip pressed too hard against the tissue. In some such catheters, as long as the catheter does not collapse, the impedance between the tip electrode and the electrode adjacent thereto (e.g., electrodes 10 and 12 in FIG. 1A) is sensitive to the contact force, but this sensitivity is drastically reduced after collapse (e.g., to the configuration shown in FIG. 1C). In such embodiments, after the collapse a good measure of the contact force may be provided by the impedance between two non-tip electrodes (e.g., electrodes 12 and 14 in FIG. 1A). Thus, in some embodiments, the contact force may be evaluated as a weighted average between contact forces evaluated for a gap between one pair of catheter electrodes, and contact force evaluated for a gap between another pair of catheter electrodes.

For example, in some embodiments, the contact force between a catheter and a tissue is evaluated based on $Z_{12}$ alone if the contact force calculated based on $F_{23}$ alone is smaller than a first threshold. In some such embodiments, the contact force is calculated based on $Z_{23}$ alone if the contact force calculated based on $F_{23}$ alone is above a second threshold. Between the two thresholds, a weighted average of the contact force calculated based on $Z_{12}$ and $Z_{23}$ is used.

In such embodiment, the contact force may be evaluated using the following equation:

$$\begin{cases} CF(Z_{12}) & \text{If } CF(Z_{23}) \le T_1 \\ CF(Z_{23}) & \text{If } CF(Z_{23}) \ge T_2 \\ CF(Z_{23})\dfrac{CF(Z_{23}) - T_1}{T_2 - T_1} + CF(Z_{12})\dfrac{CF(Z_{23}) - T_2}{T_1 - T_2} & \text{otherwise} \end{cases}$$

Wherein CF stands for contact force; $CF(Z_{ij})$ is contact force calculated based on $Z_{ij}$ alone, and $T_1$ and $T_2$ are the thresholds. $Z_{12}$ is the impedance evaluated for the gap between electrode 1, which is the tip electrode and electrode 2, which is the electrode adjacent to the tip electrode, and $Z_{23}$ is the impedance evaluated for the gap between electrode 2 and electrode 3, which is the electrode adjacent to electrode 2 (other than electrode 1). The impedances may be evaluated based on voltage readings and additional information as described above; and the contact forces may be estimated based on the impedances using predetermined parametric functions as described above.

Contact Angle

The contact angle may be roughly estimated, in some embodiments, based on the resistivity of paths connecting different catheter electrodes (201 and 202) to the reference electrode (230). While tip electrode 10 touches the tissue regardless of the angle between the catheter and the tissue (cf. FIGS. 1A-1C), the connection of the other electrodes to the tissue depends on the contact angle. For example, in FIG. 1A only tip catheter 10 touches tissue 4 and in FIG. 1C all the catheter electrodes touch tissue 4. In FIG. 1B, electrode 12 does not touch tissue 4, but is influenced from the tissue more than in FIG. 1A (and less than in FIG. 1C). Thus, the resistivity of a path connecting a non-tip electrode (e.g., electrode 12) to the reference electrode may serve as an indicator to the contact angle. In the nomenclature of FIG. 2A this path has an impedance Y, so its electrical resistivity is Re(Y). Thus, in some embodiments, the resistivity of a non-tip electrode may be used as an indicator to the contact angle.

In some embodiments, the indicator of the contact angle may be a difference or ratio between Re(Y) and Re(X), so that CAI=Re(Y)–Re(X) or CAI=Re(Y)/Re(X), where CAI stands for contact angle indicator. Measuring X and Y at various contact angles may reveal a range of CAI values at which the contact angle is of the kind illustrated in FIG. 1A (e.g., the contact angle is 0±45°) or of the kind illustrated in FIG. 1C (e.g., the contact angle is 90°±45°).

In some embodiments, the impedances X and Y may be evaluated based on the same measurements used for evaluating the impedance Z in the above-described embodiments that do not use as additional information the values of X and Y or an equality between them. The equations to be solved for evaluating Z are also suitable for evaluating X and Y.

Tissue Imaging and Tissue Properties

In some embodiments, the impedance measurements may be interpreted to indicate tissue properties and/or used for tissue imaging. For example, the impedance measurements may be indicative of tissue properties such as wall thickness, ablation transmurality and/or contiguity, air-volumes (or other characteristics) behind the wall of a heart chamber (or other volume in which the impedance is measured), blood flow in the vicinity of the electrodes, directionality of electrical conductance, tissue kind, etc. Tissue kind may include, for example, scar, fibrosis, inflammation, muscle, fat, cartilage, tendon, etc. The knowledge of any one or more of these properties may assist in tissue imaging and/or be incorporated into a tissue image, e.g., as a presentation of the measured property.

To tell tissue properties, experiments may be carried out and impedances measured, optionally at a plurality of frequencies. In the experiments, impedances may be measured when the electrodes contact tissues having different values of one property, while the other properties are controlled. For example, impedance of tissue of different thicknesses or kinds may be measured at a constant contact force, or at several controlled contact force levels. Several impedances may be measured at each experiment: impedances between different electrode pairs, and impedances at different frequencies. This way, for a given tissue property (e.g., thickness) there may be a distinct impedance vector for each property value (e.g., one impedance vector for thickness of 1 mm, second impedance vector for thickness of 2 mm etc.). Impedance vector is a term used herein for a series of impedance measurements between different electrodes and at different frequencies. Relationships between the value of the property and the measured impedance vectors may be revealed using machine learning algorithms, physical models, or combinations of physical models and machine learning.

For example, a tissue may be modeled as a plurality of stacked layers, and each of the layers may be modeled by a resistor connected serially to a capacitor. The layers may be connected to one another in parallel. Assuming that each layer is characterized by the same impedance the impedance of the entire layer may be a function of the number of layers stacked together, and thus also a function of the thickness. Based on this model, and basic physics (e.g., the superposition theorem) equations connecting impedance and tissue thickness may be written and solved using measured impedances to find tissue thickness. Tissue transmurality may be evaluated by comparing tissue thickness at a center of a lesion and at a periphery thereof.

In another example, when the electrical field goes to the reference surface electrode through the lungs, lung volume change due to breathing may change the values solved for impedances X and Y (cf. FIG. 2A). Thus, monitoring X and Y may provide respiration rate and depth.

The great difference in impedance between blood and air may also allow sensing when an air column is adjacent the heart-chamber wall, the impedance of which is being measured. This may allow identifying when the esophagus is in vicinity to the wall at the point measured by the catheter.

In one example, a machine is trained to identify tissue kind (or other tissue property) using impedance vectors measured for tissues of different kinds while keeping other properties and contact force constant. Training allows differentiating between tissues of different kinds even in absence of a physical model. A rough physical model, however, may improve differentiating between the different tissues provided training measurements of a given noise level. The training results in an algorithm that associates each impedance vector to a property type. Then, this algorithm may be used for inferring tissue type (of unknown tissue) from measured impedance vectors.

In some embodiments, the training is made with measurements where two or more of the tissue properties are unknown, and the algorithm can find property-pairs, for example, telling from an impedance vector the kind and thickness of a given tissue.

In some embodiments, the catheter may contact a large area of heart chamber wall, e.g., the entire inner wall of the left atrium, and provide data on tissue kind and/or thickness at different locations of the electrodes. In some embodiments, this may be achieved with an ablation catheter, diagnostic catheter, or any other catheter that has two or more electrodes and may move to contact different wall portions of the heart chamber. The locations of the electrodes during the movement may be provided by methods used for guiding navigation, for example, as described in International patent application PCT/IB2018/050192 filed Jan. 12, 2018.

In some embodiments, the catheter may contact a large area concurrently. For example, the catheter may be a multi-electrode basket catheter and comprise 20 or more electrodes, e.g., 20, 30, 40, 50, 60, 120, 240, or any intermediate number of electrodes. The basket may be opened in the heart chamber so that all (or many of) the electrodes contact the inner wall of the heart chamber. Data on impedance measured at multiple frequencies between neighboring pairs of these electrodes may allow reconstructing an image of the inner wall of the heart chamber showing different tissue types with different visual characteristics (e.g., color and/or texture), tissue thickness in 3D-like rendering, etc.

An Apparatus for Evaluating Contact Force

An aspect of some embodiments of the invention includes an apparatus connectible to a catheter that carries at least two catheter electrodes. The apparatus allows evaluating contact force of the catheter with a tissue. In some embodiments, the apparatus includes an electrical field generator/measurer 270, e.g., as illustrated in any one of FIGS. 2B to 2D, and a processor (e.g., processor 280 of FIG. 2A) configured to carry out methods 300 and 400.

Figure 6:
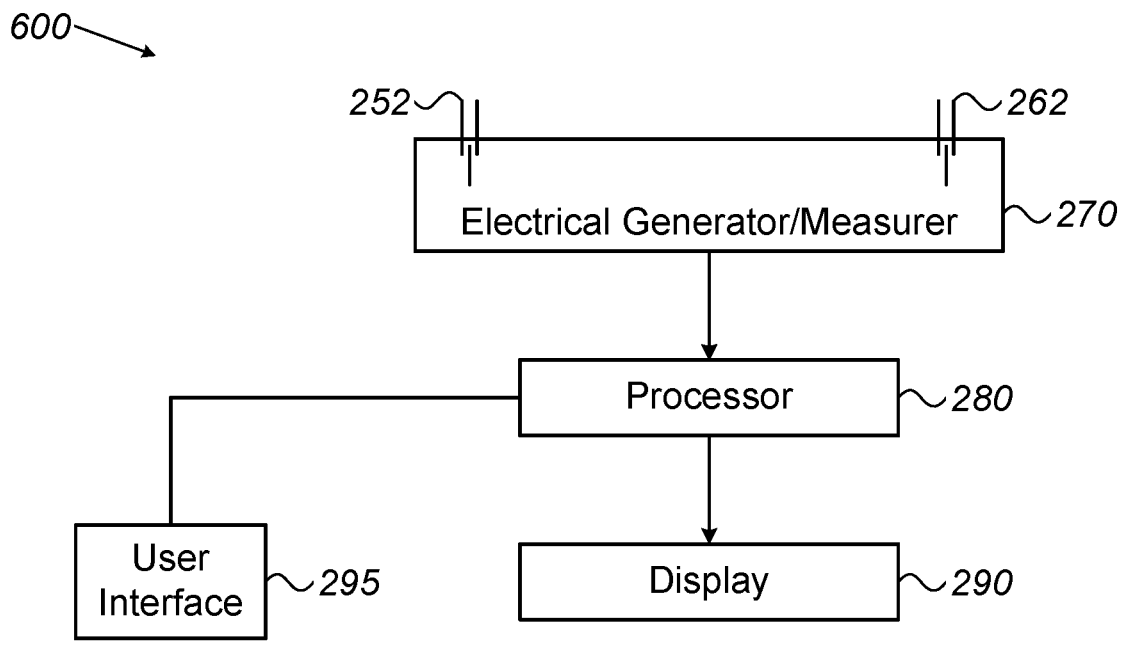
FIG. 6 is a diagrammatic illustration of an apparatus for evaluating impedance according to some embodiments of the invention.

FIG. 6 is a diagrammatic illustration of an apparatus 600 connectible to a catheter that carries at least a first catheter electrode and a second catheter electrode according to some embodiments of the invention.

Apparatus 600 includes an electrical generator/measurer 270 configured to generate one or more electrical currents and measure at least two voltage so as to allow evaluation of the impedance between two of the catheter electrodes. In some embodiments, electrical generator/measurer is configured as shown in one of FIGS. 2B to 2E.

Apparatus 600 is illustrated as configured to connect to two electrodes, via connectors 252 and 262, but may be similarly connected to additional electrodes, for example, to three electrodes, which may allow measuring impedances between three electrode pairs.

Apparatus 600 also includes a processor 280. In some embodiments, processor 280 may be configured to control components of electrical generator/measurer 270. For example, in embodiments that use time sharing (e.g., as illustrated in FIGS. 2C and 2D), processor 280 may control the switches governing the time sharing (e.g., switches 215 and 225). In some embodiments, processor 280 may be configured to control the electrical source(s)

Processor 280 is configured to receive voltage readings from the voltmeter(s) included in electrical generator/measurer 270; and evaluate an electrical impedance of a gap between the first and second catheter electrodes based on the received readings, for example, by executing a method described in relation to FIG. 3. In some embodiments, for example, time-sharing embodiments, the processor receives, in addition to the readings of the voltmeter, data indicative to the state of the switches and when each of the readings was read.

In some embodiments, processor 280 also estimates another quantity based on the evaluated impedance. The other entity may be, for example, a contact force between the catheter and a tissue, the contact angle between them, a tissue property, etc.

In some embodiments, processor 280 outputs the evaluated impedance value and/or the value of the other quantity to an output device 290, which may include, for example, a screen and/or a loudspeaker. The screen may provide visual indication (e.g., numerical or graphical) to the evaluated impedance and/or to a value of a quantity estimated based on the evaluated impedance. The speaker may provide, in some embodiments, an alarming audible signal when the impedance and/or the other quantity is at a predetermined range (e.g., when a contact force is above some safety limit).

Processor 280 is configured to receive readings from the voltmeter(s) included in electrical generator/measurer 270; and evaluate an electrical impedance of a gap between the first and second catheter electrodes based on the received readings, for example, by executing a method described in relation to FIG. 3. In some embodiments connectible to more than two electrodes, the processor may be configured to evaluate an impedance for a gap between each two of the electrodes, for example, when the number of electrodes is 4, the number of impedances may be 6. In some embodiments, impedance between only some of the pairs is being evaluated.

In some embodiments, processor 280 also estimates another quantity based on the evaluated impedance. The other entity may be, for example, a contact force between the catheter and a tissue, the contact angle between them, etc. It is noted that parameters in a parametric function connecting the evaluated impedance value to another quantity (e.g., the parameters a and b connecting the evaluated impedance to contact force, as discussed above) may be different for each pair of catheter electrodes.

In some embodiments, processor 280 outputs the evaluated impedance value to an output device 290, which may include, for example, a screen and/or a loudspeaker. The screen may provide visual indication (e.g., numerical or graphical) to the evaluated impedance and/or to a value of a quantity estimated based on the evaluated impedance. The speaker may provide, in some embodiments, an alarming audible signal when the impedance and/or the other quantity is at a predetermined range (e.g., when a contact force is above some safety limit).

Apparatus 600 may also include, in some embodiments, a user interface 295, which allows a physician to determine how processor 280 should operate, for example, at what contact forces an alarm is to be voiced, what other properties are to be displayed on output device 290. In some embodiments, user interface 295 may also provide the processor with additional information, such as the kind of catheter being used, etc.

Contact Angle Using Three or More Electrodes

As described above, in some embodiments, each of a plurality of catheter electrodes transmits to a center ground patch electrode placed on the individual's right leg. The impedance values X and Y (FIG. 2A) measured between respective catheter electrodes and the ground patch electrode are subtracted or used in a ratio to determine a contact angle indicator CAI. Accordingly, that approach relies on a difference between impedance values X and Y. Further, in that approach, the solution used to determine the CAI may be based on a relationship of six variables or values, including: I1, I2, V(1,1), V(1,2), V(2,1), and V(2, 2), wherein I1 and I2 are the currents generated for the first catheter electrode 201 and second catheter electrode 202, respectively, and V(i, j) represents a voltage measured by catheter electrode i at the frequency of catheter electrode j.

However, by making assumptions related to the voltages, currents, and impedances of the circuit, a different approach can be used to determine contact angle that does not rely on a difference between X and Y, and that does not depend on the six variables. For example, in some embodiments, it is assumed that X=Y, and that both X and Y are far greater than Z. These assumptions may be considered valid because, for example, the distance between catheter electrodes (e.g., 201, 202) is much smaller than the distances X, Y measured between the catheter electrodes 201, 202, and the ground patch electrode 230 placed on the individual's right leg. Further, I1 and I2 may be assumed to be stable and are thus not used to determine Z.

Based on the assumptions described above and by emitting electrical signals of different frequencies from each electrode, an interelectrode impedance Z can be determined using two voltages, as opposed to the six variables stated above. For example V(1,1), and V(1,2) can be used, where V(1,1) is the voltage measured by the first electrode 201 at the frequency of the first electrode 201, and V(1,2) is the voltage measured by the first electrode 201 at the frequency transmitted by the second electrode 202. The electrical signals (e.g., voltages) emitted by the electrodes 201, 202 may be generated by the electrical field generator 270. By calculating the interelectrode impedance Z using these voltages, a different approach may be used to determine contact angle in which three electrodes are used rather than two. In that regard, and as described further below, multiple interelectrode impedances (e.g., $Z_{12}$, $Z_{23}$) associated with different electrode pairs can be calculated to estimate the contact angle.

Figure 7:
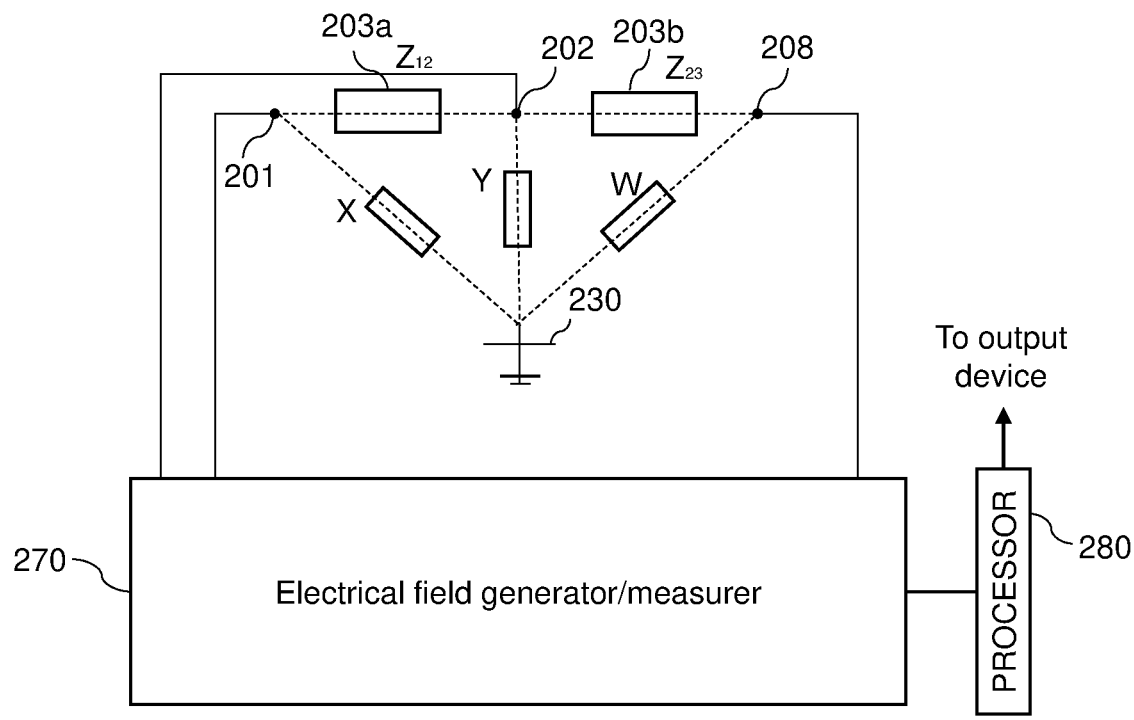
FIG. 7 is an electrical diagram of a circuit for estimating a contact angle of a catheter using three catheter electrodes based on measurements of electrical voltages according to some embodiments of the invention.

FIG. 7 is an electrical diagram showing a circuit for using three electrodes to determine contact force by computing two contact force values CF1 and CF2. For example, the contact angle may be estimated using information from three electrodes 201, 202, 208 of a catheter positioned within the body of an individual. The circuit shown in FIG. 7 may be similar to the circuit shown in FIG. 2A and described above, but additionally includes a third electrode 208 and an additional impedance W associated with the path between the third electrode 208 and the reference electrode 230. The circuit in FIG. 7 can be used to determine contact force and contact angle, but using three catheter electrodes and the assumptions that X=Y=W, and X, Y, W>>Z.

Referring to FIG. 7, a first interelectrode impedance $Z_{12}$ can be determined for the electrode pair 201-202 using the voltage values V(1,1) and V(1,2), which may be generated and/or measured using the electrical field generator/measurer 270. Similarly, a second interelectrode impedance $Z_{23}$ can be determined for the electrode pair 202-208 using the voltage values V(2,2) and V(2,3), where V(2,2) is the voltage measured at electrode 202 at the frequency of the electrode 202, and V(2,3) is the voltage measured at electrode 202 at the frequency of the electrode 208. As described further below, the interelectrode impedances $Z_{12}$ and $Z_{23}$ can be used to determine the contact angle of the catheter relative to the tissue by calculating and comparing model contact force values based on $Z_{12}$ and $Z_{23}$.

Figure 8:
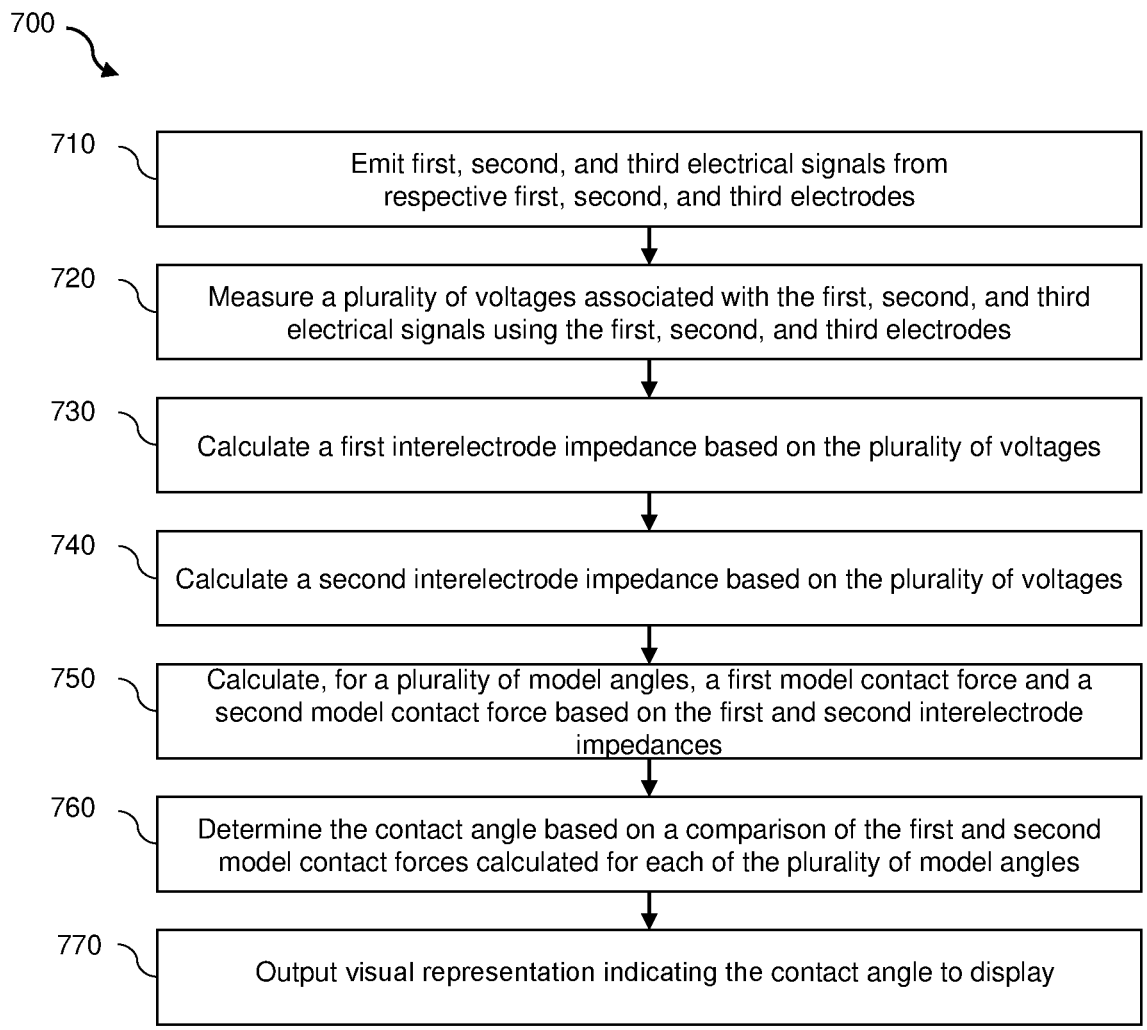
FIG. 8 is a flowchart of a method of estimating contact force between cardiac tissue of an individual and a catheter using three electrodes according to some embodiments of the invention.

FIG. 8 is a flow diagram illustrating a method 700 for calculating the contact angle of a catheter using three electrodes. It will be understood that one or all of the steps of the method 700 may be performed using a processor circuit, which may include the processor 280 and electrical field generator/measurer 270 shown in, for example, FIGS. 2A, 6, and 7. Further, the processor circuit may comprise one or more of the components of the processor circuit 150 shown in FIG. 11 and described below.

Referring to FIGS. 7 and 8, in step 710, a first electrode 201 emits a first electrical signal at a first frequency f1, a second electrode 202 emits a second electrical signal at a second frequency f2, and a third electrode 208 emits a third electrical signal at a third frequency f3. In an exemplary embodiment, the frequencies f1, f2, and f3 are different from each other such that the processor circuit can identify and/or distinguish between the signals of each electrode. Emitting each of the first, second, and third electrical signals at a different frequency advantageously allows for all signals to be emitted and detected simultaneously, without switching or multiplexing. However, in other embodiments, two or more of the frequencies f1, f2, f3 are the same. For example, in some embodiments, time switching or multiplexing is used to distinguish between each of the electrical signals. In some embodiments, the first electrode 201, the second electrode 202, and the third electrode 208 are positioned at a distal portion of a catheter sized, shaped, and otherwise structurally arranged to be positioned within a body of an individual. In some embodiments, the catheter comprises an intracardiac electrophysiology catheter. In some embodiments, the electrodes 201, 202, 208 are controlled by a processor circuit, which may include an electrical field generator 270, to emit the first, second, and third electrical signals.

In step 720, the processor circuit controls the first, second, and third electrodes to measure a plurality of voltages. In some embodiments, the processor circuit controls the first electrode 201 to measure a first voltage at the first frequency f1 and a second voltage at the second frequency f2. Similarly, the processor circuit may control the second electrode 202 to measure a third voltage at the second frequency f2, and a fourth voltage at the third frequency f3. Further, in some embodiments, the processor circuit may control the third electrode 208 to measure voltages associated with the first frequency f1, the second frequency f2, and the third frequency f3. However, in some embodiments, each electrode may be used to measure or detect a different combination of voltages, such as the voltages associated with all three frequencies f1, f2, f3. In some embodiments, voltage measurements from only two of the three electrodes 201, 202, 208 are used to determine contact angle, such as voltage measurements from the first electrode 201 and the second electrode 202. In some embodiments, other parameters of the first, second, and third electrical signals are measured. For example, in some embodiments, the currents of the electrical signals are detected or measured in step 720, rather than the voltages. In some embodiments, both the currents and the voltages of the electrical signals are measured.

Figure 9:
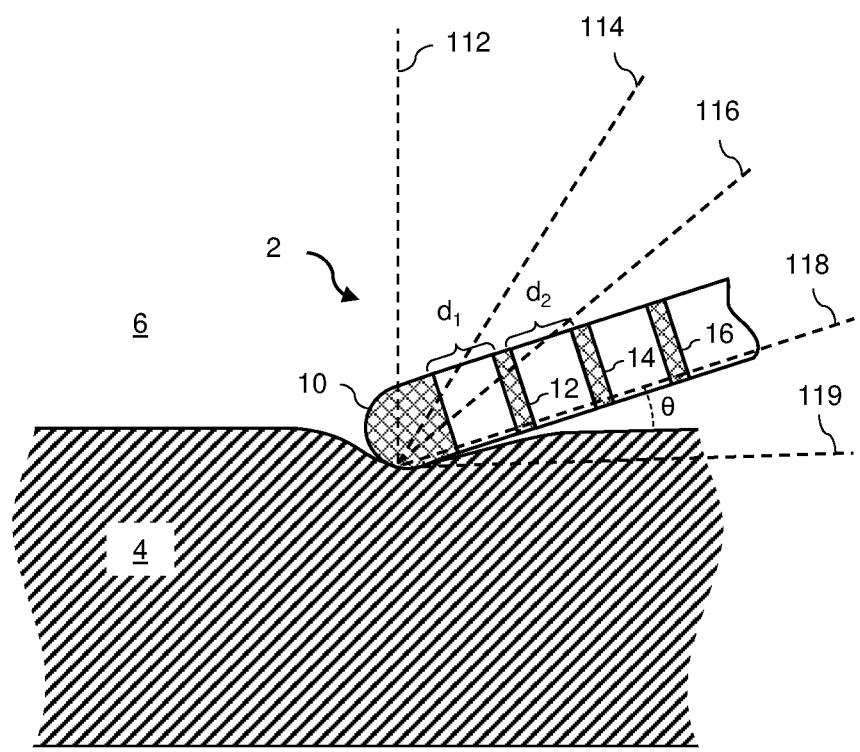
FIG. 9 is diagrammatic view of a distal end of a catheter pressed against tissue at a contact angle according to some embodiments of the invention.

Referring to FIGS. 8 and 9, in step 730, a first interelectrode impedance $Z_{12}$ of a first hypothetical load 203a is calculated. The first interelectrode impedance $Z_{12}$ is associated with a path or distance $d_1$ between a first catheter electrode 201 and a second catheter electrode 202. In step 740, a second interelectrode impedance $Z_{23}$ of a second hypothetical load 203b is calculated. The second interelectrode impedance $Z_{23}$ is associated with a path or distance $d_2$ between the second catheter electrode 202 and a third catheter electrode 208. The interelectrode impedances $Z_{12}$, $Z_{23}$ may be calculated based on respective pairs of voltages. For example, $Z_{12}$ may be calculated based on V(1,1) and V(1,2), and $Z_{23}$ may be calculated based on V(2,2) and V(2,3). The interelectrode impedances may be the impedances between any combination of the catheter electrodes (e.g., $Z_{12}$, $Z_{13}$, $Z_{23}$). Any suitable combination of interelectrode impedances can be used to determine the contact angle (e.g., $Z_{12}$ and $Z_{23}$, $Z_{12}$ and $Z_{13}$).

The paths $d_1$ and $d_2$ associated with the respective interelectrode impedances $Z_{12}$ and $Z_{23}$ are shown in FIG. 9 below, with $d_1$ extending between the first electrode 10 and the second electrode 12, and $d_2$ extending between the second electrode 12 and the third electrode 14. In some aspects, the impedances $Z_{12}$ and $Z_{23}$ may substantially differ in value based on the medium of the paths $d_1$ and $d_2$. For example, for $Z_{12}$, the first catheter electrode 10 may be in contact with the tissue, while for $Z_{23}$, both the second and the third electrodes 12, 14 are in the blood flow area 6. By calculating and comparing pairs of contact force values based on the respective interelectrode impedances $Z_{12}$ and $Z_{23}$, a contact angle can be determined. In some embodiments, an additional interelectrode impedance may be calculated between, for example, the third electrode 14 and the fourth electrode 16.

Referring to FIGS. 7 and 8, in step 750, the processor uses the calculated impedances $Z_{12}$ and $Z_{23}$ to calculate a plurality of pairs of model contact forces, where each pair of model contact forces is associated with a model contact angle, or model angle, and includes a first model contact force CF1 and a second model contact force CF2. As described further below, in an exemplary embodiment, each of the first model contact forces CF1 is calculated based on $Z_{12}$, and each of the the second model contact forces CF2 is calculated based on $Z_{23}$. A relationship between impedance Z and contact force CF can be used to translate between impedance (measured in Ohms) and contact force (measured in grams). In some aspects, impedance Z may be described as having a tissue impedance component, and a blood impedance component. For example, the relationship between the impedance Z and the contact force CF may be expressed as:

$$\frac{1}{Z} = P\frac{1}{T} + (1-P)\frac{1}{B}, \text{ where}$$
$$P = 1 - e^{-CF}$$

T represents the catheter-tissue impedance and is associated with the tissue type (muscle, cartilage, valve, septum, etc.), B represents the impedance of the blood surrounding the tissue, measured between two electrodes, and P is a parameter associated with an amount in which the catheter sinks into the tissue as the contact force increases. For P=0, the catheter is in the blood pool, and does not touch the tissue, while for P=1, the catheter if fully wrapped by the tissue (CF at maximum level).

By plotting a plurality of graphs of 1/Z vs. 1/B for different CF values, and using linear regression, the slope and intersections of the graphs can be determined and used to calculate CF based on Z. For example, the relationship between CF and Z can be described as:

$$CF = bZ^a$$

Where a is the slope of the graph for a given contact force (in grams) and b is the y-intercept of the graph. By using the relationship above with respect to two forces (e.g., 5 grams and 10 grams), a and b can be determined. Once a and b are determined, the relationship described between CF and Z described above can be used to calculate CF.

In some aspects, the catheter-tissue impedance may be expressed as:

$$Z = \beta e^{-\alpha(CF)}$$

where $\alpha$ is based on the contact angle, and $\beta$ represents parameters that describe the structure of the system, such as the distance between electrodes and the thickness of the catheter. In some embodiments, one or both of $\alpha$ or $\beta$ are pre-determined according to relationship above using known values for Z and CF. In the catheter-tissue impedance relationship, it will be understood that, as contact force increases, the impedance between the catheter and the tissue decreases. However, in practice, the relationship between Z and CF may also include a blood-catheter impedance. In some aspects, as the contact force increases, less blood surrounds the catheter as the catheter becomes increasingly wrapped in tissue. Thus, as contact force increases, the blood-catheter impedance increases. In some embodiments, the relationship between interelectrode impedance Z and contact force CF can be solved for the contact force CF by using logarithmic regression on the relationship.

Figure 10:
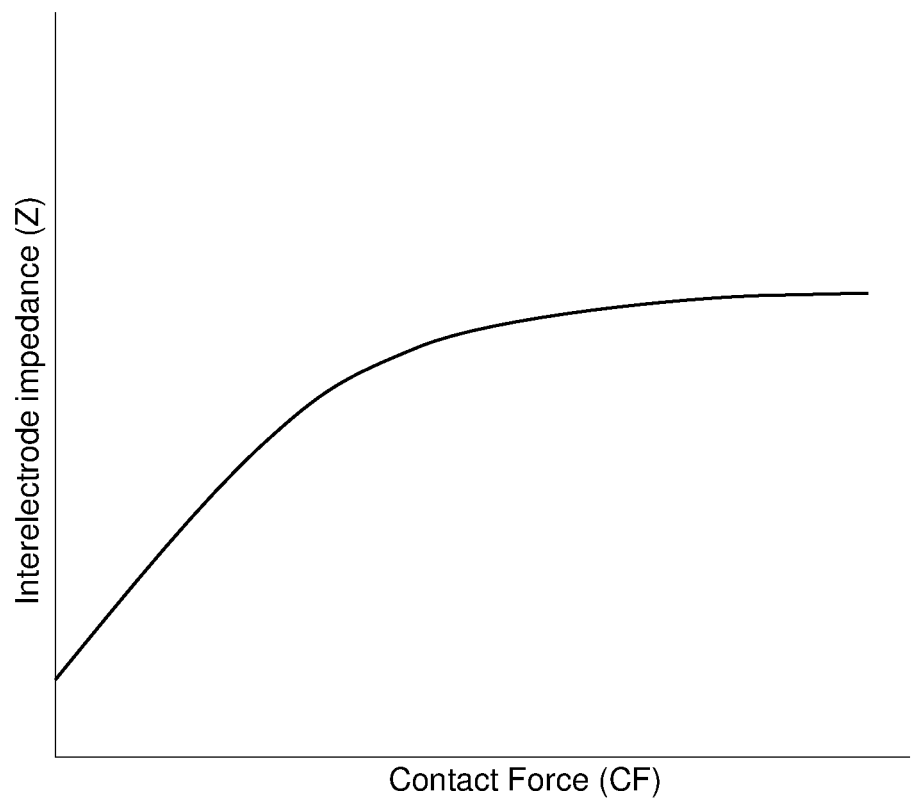
FIG. 10 is a graph illustrating a relationship between interelectrode impedance and contact force of an electrode being pressed against tissue according to some embodiments of the present disclosure.

FIG. 10 is a graphical representation of the relationship between impedance Z and contact force CF for a catheter electrode in contact with blood and tissue. In that regard, the relationship shown in FIG. 10 illustrates the cumulative effect of increases in contact force on both the catheter-tissue impedance and the blood-catheter impedance. When the contact force of an electrode is small, the impedance value climbs in a linear fashion. However, as the contact force increases, the tissue begins to surround or wrap around the electrode, and the slope or change in impedance with contact force begins to decrease. Eventually, the catheter electrode is substantially wrapped by the tissue such that the impedance value does not significantly change with increased contact force.

Referring to FIGS. 8 and 9, based on the relationship between interelectrode impedance and contact force, a plurality of pairs of model contact forces CF1 and CF2 may be calculated using, as inputs, $Z_{12}$, $Z_{23}$, and each of a plurality of model contact angles (parameter a in the equation above), such as 0°, 45°, 60°, or 90°. However, any suitable number of model contact angles can be used, including two, three, four, five, six, eight, and/or other values, both larger and smaller. Further, any suitable combination of angles can be used as inputs, including values between 0° and 90°, such as 10°, 20°, 30°, 50°, 70°, 80°, and/or any other suitable angle. The terms model is used to distinguish hypothetical contact forces calculated based on hypothetical angles from contact force measurements and contact angles representative of the actual position and orientation of the catheter. In that regard, a model used for identifying a contact angle may include a plurality (e.g., four) of model angles that may not necessarily reflect an actual angular orientation of the catheter with respect to the tissue. Thus, while many model contact forces CF1, CF2 may be calculated based on $Z_{12}$ and $Z_{23}$, some or all of the model contact forces may not be representative of the actual force applied to the tissue by the catheter, but are instead calculated in an intermediate step of estimating the actual contact angle. In some embodiments, the first model contact force and the second model contact force can be calculated using a relationship that includes the plurality of model angles, the first and second interelectrode impedances, and interelectrode spacing.

Referring again to FIG. 9, a distal end of ablation catheter 2 pressed against tissue 4 at a contact angle θ is shown. The table below includes a number of exemplary values of CF1 and CF2 calculated for the catheter configuration shown in FIG. 9 using four different hypothetical or model contact angles (0°, 45°, 60°, and 90°).

| Hypothetical Angle | CF1 (in grams) | CF2 (in grams) |
|---|---|---|
| 0° | 2.9 | 3.5 |
| 45° | 3.5 | 4.2 |
| 60° | 5.1 | 1.6 |
| 90° | 5.5 | 0.5 |

The angle θ as shown in FIG. 9 is defined by the top surface of the tissue 4 and the axis 118 of the catheter 2. Lines 112, 114, 116, and 119 represent alternative orientations of the catheter at 90°, 60°, 45°, and 0°, respectively.

Referring again to FIG. 8, in step 760, the estimated contact angle is selected or determined by comparing the calculated CF1 and CF2 values to each other for each model contact angle and selecting the model contact angle for which the calculated CF1 and CF2 are the closest to each other. In other words, it is assumed that the correct or closest model angle used as an input in calculating CF1 and CF2 will yield values for CF1 and CF2 that are the same or close to one another. As shown in the table above, a comparison of the CF1 and CF2 values for each angle shows that $|CF1_{0°}-CF2_{0°}|=0.6$, $|CF1_{45°}-CF2_{45°}|=0.7$, $|CF1_{60°}-CF2_{60°}|=3.5$, and $|CF1_{90°}-CF2_{90°}|=5.0$. Accordingly, 0° is the angle for which CF1 and CF2 are closest to one another, with 45° being the angle that yields the next closest values for CF1 and CF2. Thus, in some embodiments, 0° is output by the processor circuit as the estimated contact angle.

Further, in some embodiments, finer angular resolution can be achieved by interpolating between two, three, four, or more model angles. For example, in some embodiments, the processor circuit may interpolate between model angles using a weight function and applying a weight factor to each contact angle θ based on the value of the relationship $|CF1_θ-CF2_θ|$ for each contact angle. For example, if $|CF1_{0°}-CF2_{0°}|$ yields the smallest value, and $|CF1_{45°}-CF2_{45°}|$ yields the next smallest value, corresponding weights can be applied to the angles based on the corresponding value for $|CF1_θ-CF2_θ|$, which may result in an angle between 0° and 45° (e.g., 20°). For example, greater weight may be assigned to the angle(s) with a smaller difference between model contact forces, and lesser weight may be assigned to the angle(s) with a larger different between model contact forces. In one embodiment, the weight function applied to each model angle may be defined as:

$$\frac{1}{(CF1-CF2)^2}$$

It will be understood that, in some embodiments, the weighting function can be normalized to determine the corresponding weight factors for each angle. In some embodiments, the processor circuit may first determine the two model angles with the smallest differences between the model contact forces and then interpolate between the two model angles to determine the actual contact angle of the catheter. In step 770, a visual representation indicating the determined or estimated contact angle is output to a display. For example, the estimated contact angle may be output by the processor 280 to the display 290 (FIG. 6). In some embodiments, the visual representation comprises a numerical value of the contact angle. In some embodiments, the visual representation comprises a diagrammatic representation of the contact angle, such as an illustration or icon of a catheter contacting tissue at the contact angle. In some embodiments, the visual representation includes text indicating the contact angle. In other embodiments, the visual representation indicates the contact angle based on color, shade, or any other suitable type of visual representation.

It will be understood that various modifications can be made to the method described above with respect to FIG. 8. For example, in some embodiments, more than three electrodes are used, such as four, five, six, eight, ten, twenty, thirty, sixty, and/or other values, both larger and smaller. Any suitable number of interelectrode impedances may be calculated, including two, three, four, five, six, eight, ten, twenty, thirty, sixty, and/or other values, both larger and smaller. Further, alternative or additional combinations of voltage measurements other than those described above can be used to determine interelectrode impedances. For example, in some embodiments, Further, alternative relationships between interelectrode impedance Z and contact force CF can be used to determine the contact force values for each angle. Further still, the contact force values shown in the table above are for illustrative purposes and may not reflect values typically determined by the system.

Figure 11:
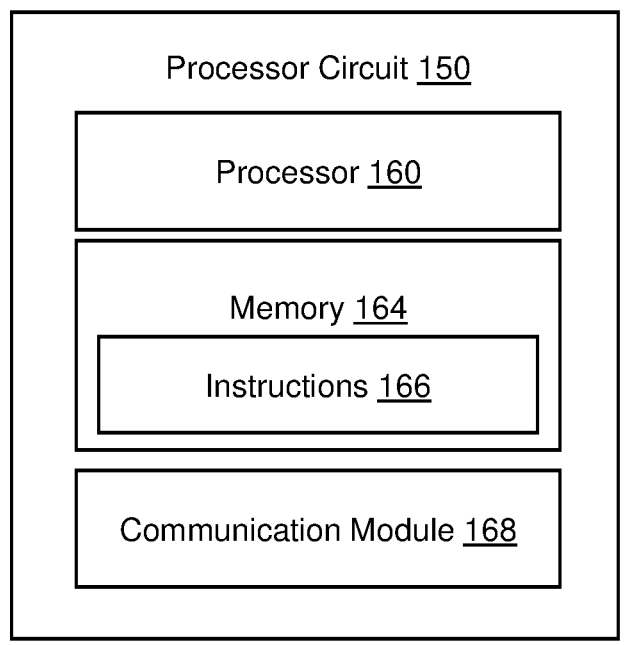
FIG. 11 is a schematic diagram of a processor circuit according to embodiments of the present disclosure.

FIG. 11 is a schematic diagram of a processor circuit 150, according to embodiments of the present disclosure. The processor circuit 150 may be implemented in the system described in FIG. 6 and/or the method 700 described in FIG. 8. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, an FPGA, another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The non-transitory computer-readable medium may store instructions. For example, the memory 164, or non-transitory computer-readable medium may have program code recorded thereon, the program code including instructions for causing the processor circuit 150, or one or more components of the processor circuit 150, to perform the operations described herein. For example, the processor circuit 150 can execute operations described with reference to FIGS. 1A-10, including the operations described with reference to the methods 300, 400, and 700. Instructions 166 may also be referred to as code or program code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements. The memory 164, with the code recorded thereon, may be referred to as a computer program product.

The communication module 168 can include any electronic circuitry and/or logic circuitry to facilitate direct or indirect communication of data between the processor circuit 150, the electrical field measurer 270, and/or the display 290. In that regard, the communication module 168 can be an input/output (I/O) device. In some instances, the communication module 168 facilitates direct or indirect communication between various elements of the processor circuit 150 and/or the system 600 (FIG. 6).

It is expected that during the life of a patent maturing from this application many relevant transcatheter treatments will be developed; the scope of the term "transcatheter delivery of a disease treatment" is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A method of determining a contact angle between a catheter and tissue within a body, the method comprising:
    emitting:
        a first electrical signal from a first electrode of the catheter,
        a second electrical signal from a second electrode of the catheter, and a third electrical signal from a third electrode of the catheter;
measuring, using the first electrode, the second electrode, and the third electrode, a plurality of voltages associated with the first electrical signal, the second electrical signal, and the third electrical signal;
calculating a first interelectrode impedance based on the plurality of voltages;
calculating a second interelectrode impedance based on the plurality of voltages;
for each angle of a plurality of hypothetical angles, calculating a set of a first hypothetical contact force for the angle and a second hypothetical contact force for the angle, wherein the first hypothetical contact force and the second hypothetical contact force are calculated based on the first interelectrode impedance and the second interelectrode impedance, respectively;
comparing the first hypothetical contact force and the second hypothetical contact force in each set and selecting an angle of the plurality of hypothetical angles based on closeness of first hypothetical contract force and the second hypothetical contact force to each other in the set of the selected angle;
determining the contact angle based on the selected angle and outputting a representation indicative of the contact angle.

2. The method of claim 1, wherein:
emitting the first electrical signal comprises emitting the first electrical signal at a first frequency,
emitting the second electrical signal comprises emitting the second electrical signal at a second frequency,
emitting the third electrical signal comprises emitting the third electrical signal at a third frequency, and
the first frequency, the second frequency, and the third frequency are different from each other.

3. The method of claim 2, wherein measuring the plurality of voltages comprises:
measuring a first voltage using the first electrode at the first frequency; and
measuring a second voltage using the first electrode at the second frequency.

4. The method of claim 3, wherein measuring the plurality of voltages comprises:
measuring a third voltage using the second electrode at the second frequency; and
measuring a fourth voltage using the second electrode at the third frequency.

5. The method of claim 1, wherein calculating the first hypothetical contact force and the second hypothetical contact force comprises calculating the first hypothetical contact force and the second hypothetical contact force using a relationship that includes the plurality of hypothetical angles, the first interelectrode impedance, the second interelectrode impedance, and interelectrode spacing.

6. The method of claim 1, wherein determining the contact angle comprises interpolating two or more hypothetical angles by applying a weight function to each of the plurality of hypothetical angles based on a comparison of the first hypothetical contact force and the second hypothetical contact force for each of the plurality of hypothetical angles.

7. An apparatus, comprising:
an electrical generator and measurer;
a processor circuit in communication with a catheter configured to contact tissue within a body at a contact angle, wherein the processor circuit is configured to:
control the electrical generator and measurer to:
emit from a first electrode of the catheter a first electrical signal,
emit from a second electrode of the catheter a second electrical signal,
emit from a third electrode of the catheter a third electrical signal; and
measure using the first electrode, the second electrode, and the third electrode a plurality of voltages associated with the first electrical signal, the second electrical signal, and the third electrical signal;
calculate a first interelectrode impedance based on the plurality of voltages;
calculate a different, second interelectrode impedance based on the plurality of voltages;
for each angle of a plurality of hypothetical angles, calculate a set of a first hypothetical contact force for the angle and a second hypothetical contact force for the angle, wherein the first hypothetical contact force and the second hypothetical contact force are calculated based on the first interelectrode impedance and the second interelectrode impedance, respectively;
compare the first hypothetical contact force and the second hypothetical contact force in each set and select an angle of the plurality of hypothetical angles based on closeness of first hypothetical contract force and the second hypothetical contact force to each other in the set of the selected angle;
determine the contact angle based on the selected angle; and
output a representation indicative of the contact angle.

8. The apparatus of claim 7, wherein the processor circuit is configured to control the electrical generator and measurer to:
emit, from the first electrode, the first electrical signal at a first frequency;
emit, from the second electrode, the second electrical signal at a second frequency; and
emit, from the third electrode, the third electrical signal at a third frequency,
wherein the first frequency, the second frequency, and the third frequency are different from each other.

9. The apparatus of claim 8, wherein the processor circuit is configured to control the electrical generator and measurer to:
measure, using the first electrode, a first voltage at the first frequency, and
measure, using the first electrode, a second voltage at the second frequency.

10. The apparatus of claim 9, wherein the processor circuit is configured to control the electrical generator and measurer to:
measure, using the second electrode, a third voltage at the second frequency, and
measure, using the second electrode, a fourth voltage at the third frequency.

11. The apparatus of claim 7, wherein the processor circuit is configured to calculate the first hypothetical contact force and the second hypothetical contact force using a relationship that includes the plurality of hypothetical angles, the first interelectrode impedance, the second interelectrode impedance, and interelectrode spacing.

12. The apparatus of claim 7, wherein the processor circuit is configured to determine the contact angle by interpolating two or more hypothetical angles.

13. The apparatus of claim 7, wherein the catheter comprises an intracardiac electrophysiology catheter, and wherein the first electrode, the second electrode, and the third electrode are positioned at a distal portion of the catheter.

14. The apparatus of claim 7, further comprising:
the catheter comprising the first electrode, the second electrode, and the third electrode positioned at a distal portion of the catheter.

15. A non-transitory computer-readable storage medium having stored a computer program comprising instructions, which, when executed by a processor, cause the processor to:
emit:
 a first electrical signal from a first electrode of the catheter,
 a second electrical signal from a second electrode of the catheter, and
 a third electrical signal from a third electrode of the catheter;
measure, using the first electrode, the second electrode, and the third electrode, a plurality of voltages associated with the first electrical signal, the second electrical signal, and third third electrical signal;
calculate a first interelectrode impedance based the plurality of voltages;
calculate a second interelectrode impedance based on the plurality of voltages;
calculate, for each angle of a plurality of hypothetical angles, a set of a first hypothetical contact force for the angle and a second hypothetical contact force for the angle, wherein the first hypothetical contact force and the second hypothetical contact force are calculated based on the first interelectrode impedance and the second interelectrode impedance, respectively;
compare the first hypothetical contact force and the second hypothetical contact force in each set and select an angle of the plurality of hypothetical angles based on closeness of first hypothetical contract force and the second hypothetical contact force to each other in the set of the selected angle;
determine the contact angle based on the selected angle; and
output a representation indicative of the contact angle.

* * * * *